US007915324B2

(12) United States Patent
Eckert et al.

(10) Patent No.: US 7,915,324 B2
(45) Date of Patent: *Mar. 29, 2011

(54) DENTAL COMPOSITION CONTAINING UNSATURATED CARBOSILANE CONTAINING COMPONENTS

(75) Inventors: Adrian S. Eckert, Munich (DE); Peter Bissinger, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 952 days.

This patent is subject to a terminal disclaimer.

(21) Appl. No.: 11/572,069

(22) PCT Filed: Jul. 14, 2004

(86) PCT No.: PCT/EP2004/007746
§ 371 (c)(1), (2), (4) Date: Jan. 12, 2007

(87) PCT Pub. No.: WO2006/005363
PCT Pub. Date: Jan. 19, 2006

(65) Prior Publication Data
US 2007/0207443 A1 Sep. 6, 2007

(51) Int. Cl.
*A61K 6/083* (2006.01)
*A61C 5/00* (2006.01)

(52) U.S. Cl. .......... 523/116; 528/32; 528/43; 433/228.1
(58) Field of Classification Search .................. 523/116; 528/32, 43; 433/228.1
See application file for complete search history.

(56) References Cited

U.S. PATENT DOCUMENTS

| | | | |
|---|---|---|---|
| 3,715,334 A | 2/1973 | Karstedt | |
| 3,775,352 A | 11/1973 | Leonard | |
| 3,814,730 A | 6/1974 | Karstedt | |
| 3,927,116 A | 12/1975 | Rick et al. | |
| 3,933,880 A | 1/1976 | Bergstrom et al. | |
| 3,971,754 A | 7/1976 | Jurecic | |
| 4,391,590 A | 7/1983 | Dougherty | |
| 4,704,438 A | 11/1987 | Niwa et al. | |
| 4,767,798 A | 8/1988 | Gasser et al. | |
| 4,788,268 A | 11/1988 | Lau et al. | |
| 5,145,886 A | 9/1992 | Oxman et al. | |
| 5,165,890 A | 11/1992 | Discko | |
| 5,233,006 A | 8/1993 | Wolter et al. | |
| 5,322,440 A | 6/1994 | Steele | |
| 5,367,001 A | 11/1994 | Itoh et al. | |
| 5,691,433 A | 11/1997 | Kotani et al. | |
| 6,046,250 A | 4/2000 | Boardman et al. | |
| 6,245,828 B1 | 6/2001 | Weinmann et al. | |
| 6,335,413 B1 | 1/2002 | Zech et al. | |
| 6,376,569 B1 | 4/2002 | Oxman et al. | |
| 6,566,413 B1 | 5/2003 | Weinmann et al. | |
| 6,624,236 B1 | 9/2003 | Bissinger et al. | |
| 6,653,375 B2 | 11/2003 | Moszner et al. | |
| 6,852,822 B1 | 2/2005 | Bissigner et al. | |
| 7,576,144 B2 * | 8/2009 | Lewandowski et al. ...... 523/115 |
| 2002/0082315 A1 | 6/2002 | Moszner et al. | |
| 2003/0035899 A1 | 2/2003 | Klettke et al. | |
| 2003/0166816 A1 | 9/2003 | Bissinger et al. | |
| 2004/0110863 A1 | 6/2004 | Zech et al. | |

FOREIGN PATENT DOCUMENTS

| | | |
|---|---|---|
| EP | 0 238 025 A2 | 9/1987 |
| EP | 0 451 709 A2 | 10/1991 |
| EP | 1 368 402 A1 | 8/2004 |
| EP | 1 512 724 A1 | 9/2005 |
| WO | WO 86/01219 * | 2/1986 |
| WO | WO 00/38619 | 7/2000 |
| WO | WO 01/07444 A1 | 2/2001 |
| WO | WO 01/92271 A1 | 12/2001 |
| WO | WO 01/95862 A1 | 12/2001 |
| WO | WO 02/066535 A1 | 8/2002 |
| WO | WO 2006/005363 A1 | 1/2006 |
| WO | WO 2006/005366 A1 | 1/2006 |
| WO | WO 2006/005368 A1 | 1/2006 |

OTHER PUBLICATIONS

Beck, H., N., Chaffee, R., G., Phenenyl Silicon Compounds, J. Chem. Eng. Data 1963, 8(3), 453-454.
Houben-Weyl, Methoden d. Organ. Chemie, vol. VI/3, p57 (1st preparation example) or p56 (1st prep. example), Georg Thieme Verlag, Stuttgart, 1965, 4. edition.
Houben-Weyl, Methoden d. Organ. Chemie, vol. XIII/2a, p47ff., Georg Thieme Verlag, Stuttgart, 1973, 4. edition.
Marciniec, B., Comprehensive Handbook on Hydosilylation, Pergamon press, Oxford, 1992.
Marciniec, B., Comprehensive Handbook on Hydrosilylation, p8ff, Pergamon Press, Oxford, 1992.
Marciniec, B., Comprehensive Handbook on Hydrosilylation,p107ff., Pergamon Press, Oxford, 1992.
Tarbell, D., S., Wilson, J., W., The Rearrangement of 4-Crotyloxy-3,5- Dichlorobenzoic Acid, J.Am.Chem.Soc. 1942, 64(5), 1066-1070.
DIN EN ISO 4049 2001.
DIN EN ISO 9917-1 2004.
DIN EN ISO 9917-2 1999. European Office Communication Pursuant to Article 94(3) EPC dated Feb. 19, 2010; 3 pgs.
International Preliminary Report on Patentability and Written Opinion for PCT/EP2004/007746; 6 pgs. 2005.
"Acrylate" [online], Wikimedia Foundation, Inc., San Francisco, CA, page last modified Jul. 7, 2010, retrieved from the internet on Aug. 23, 2010 at <URL: http://en.wikipedia.org/wiki/Acrylate>; 1 pg.
"Acrylic acid" [online], Wikimedia Foundation, Inc., San Francisco, CA, page Last modified Aug. 16, 2010, retrieved from the internet on Aug. 23, 2010 at <URL:http://en.wikipedia.org/wiki/Acrylatic_acid>; 3 pgs.
"Acryloyl group" [online], Wikipedia Foundation, Inc., San Francisco, CA, page last modified Aug. 15, 2010, retrieved from the internet on Aug. 23, 2010 at <URL:http://en.wikipedia.org/wiki/Acryloyl_group>; 1 pg.

* cited by examiner

*Primary Examiner* — Tae H Yoon
(74) *Attorney, Agent, or Firm* — Sean Edman; Pamela Stewart

(57) ABSTRACT

The invention relates to a dental composition comprising a) carbosilane containing component (A) comprising at least 1 Si-Aryl bond, at least 1 silicon atom, at least 1 unsaturated moiety, no Si-Oxygen bond, b) initiator (B), c) optionally filler (C) and d) optionally component (D) selected from modifiers, dyes, pigments, thixotropic agents, flow improvers, polymeric thickeners, surfactants, odorous substances, diluting agent(s) and flavouring.

19 Claims, No Drawings

DENTAL COMPOSITION CONTAINING UNSATURATED CARBOSILANE CONTAINING COMPONENTS

CROSS REFERENCE TO RELATED APPLICATIONS

This application is a national stage filing under 35 U.S.C. 371 of PCT/EP2004/007746, filed Jul. 14, 2004.

The present invention relates to a curable dental composition containing an unsaturated carbosilane component. The composition has improved properties and can be used e.g. as a dental filling material.

The dental filling materials on the market can generally be divided into composites, resin modified glass ionomer cements and glass ionomer cements (GIZ). The composites cure usually via a light induced radical polymerisation of unsaturated components, especially (meth)acrylates. The glass ionomer cements cure by a cement setting reaction, whereas the resin modified glass ionomer cements both curing is achieved using both mechanisms.

Of special interest are the dental composites, the curing of which results in a very hard material compared to the glass ionomer cements which is especially useful for filling teeth cavities. However, a well known disadvantage of the dental composites on the market is that the compositions shrink on curing. A further drawback is, that some of the components of the dental composite materials are not hydrolytically very stable and/or comparable hydrophilic. Thus harmful substances can emerge from the cured composition over the years.

Attempts were made to solve the above mentioned problems.

In this respect U.S. Pat. No. 6,653,375 B2 describes urethane di(meth)acrylate derivatives of 1,3-bis(1-isocyanato-1-1methylethyl)benzene. It is stated that the monomers have a refractive index compatible with that of customary dental filling materials, do not tend towards discolorations and can replace bis-GMA in dental materials without impairing the mechanical properties of the materials.

U.S. Pat. No. 6,624,236 B1 is directed to cyclosiloxane-based crosslinkable monomers, production thereof and use thereof in polymerisable materials, in particular to polysiloxanes from sol-gel-condensable cyclosiloxane (meth)acrylates as well as resinous compositions.

U.S. Pat. No. 6,566,413 B1 relates to polymerisable materials based on hardenable siloxane compounds useful for dental compositions. It is described that the siloxane compounds used display a low viscosity, permit a high filler uptake and lead to compositions with a low polymerisation shrinkage.

In WO 01/92271 A1 prepolymeric (meth)acrylates with polycyclic or aromatic segments are described useful for the preparation of dental materials. It is said that the siloxane monomers have a high molecular weight (e.g. over 600 g/mol), have a high (meth)acrylate functionality and a low viscosity.

WO 01/095862 A1 refers to a low shrinking polymerisable dental material including a mixture of di- or poly(meth)acrylate, an alkoxylated bisphenol dimethacrylate, a polymerisable monomer, a polymerisation initiator and/or sensitizer, a stabilizer and a filler. It is mentioned that the volumetric shrinkage during polymerisation is less than 2 Vol-%.

EP 0 451 709 A2 describes silanes of a certain formula which can comprise groups containing (meth)acrylate moieties. It is stated that the silanes can be used as such or as additives for coating compositions, bulk materials, adhesives and compositions for injection moulding.

The solutions described above however are not completely satisfying.

Therefore, there is a need for alternatives. There is especially a need for alternative materials with improved properties.

It is thus an object of the present invention to alleviate one or more of the problems mentioned above.

It is also an object of the present invention to provide a composition with esthetical properties, which is useful in the dental field.

It is another object of the present invention to provide a lipophilic composition.

It is another object of the present invention to provide a composition with improved properties, especially a composition which enables one to provide a composition having a low shrinkage value.

It has been found that one or more of the above mentioned objects can be achieved by providing a composition as described in the text below.

Surprisingly, it has been found that using aromatic carbosilane containing components comprising polymerisable groups such as (meth)acrylates and not containing carbosiloxane structures enables one to provide curable dental compositions with improved properties.

Thus, the invention relates to a dental composition comprising
a) carbosilane containing component (A) comprising
   at least 1 Si-Aryl bond,
   at least 1 silicon atom,
   at least 1 unsaturated moiety;
   no Si—Oxygen bond
b) initiator (B);
c) optionally filler (C);
d) optionally component (D) selected from modifiers, dyes, pigments, thixotropic agents, flow improvers, polymeric thickeners, surfactants, odorous substances, diluting agent(s) and flavourings.

The present invention also relates to a method of producing the composition as described below.

Additionally, the present invention relates to a method of using the composition as described below.

Carbosilane containing component (A) can be used alone or in a mixture with other (meth)acrylate functional components as reactive compounds in dental materials that may also contain other reactive and/or unreactive compounds, if needed.

Carbosilane containing component (A) usually shows a comparably high refractive index together with a comparably low viscosity so that the dental compositions provided usually have a good opacity and thus are highly esthetic. Moreover, the compositions usually show comparably low shrinkage as well as low uptake of water and/or water soluble dyes (e.g. from coffee, tea, red wine) after curing compared to other dental compositions on the market.

The terms "comprise" and "contain" within the meaning of the invention introduce a non exhaustive list of features. Likewise, the word "one" or "a" is to be understood in the sense of "at least one".

The term "dental composition" according to the invention is a curable composition to be used in the dental field for different purposes, usually in small amounts of a few grams.

The term "initiator" according to the invention is a substance or mixture of substances capable of starting a curing reaction, preferably a radical curing reaction.

The term "unsaturated moiety" according to the invention refers to a moiety which is polymerisable, especially radically polymerisable, comprising preferably a (meth)acrylate group.

The term "aryl" according to the invention refers to an aromatic moiety (e.g. comprising $C_6$ to $C_{14}$ carbon atoms), preferably phenyl, naphthyl, alkoxyphenyl, alkoxy naphthyl, bisphenol A ethers, bisphenol F ethers. Besides an attached Si-Atom, the aryl moiety can bear 1 or 2 substituents, preferably alkyl and/or aryl ether groups (e.g. $C_{1-8}$ alkyl, $C_{2-10}$ alkenyl, $C_{3-6}$ cycloalkyl, $C_{4-6}$ cycloalkenyl, $C_{6-10}$ aryl).

Carbosilane containing component (A) can be synthesized e.g. via a hydrosilylation reaction (cf. Marciniec, B., Comprehensive Handbook on Hydrosilylation, Pergamon Press, Oxford, 1992).

The hydrosilylation reaction is an addition reaction where a SiH functional component (i) is added to an olefinic functional component (ii) in the presence of a catalyst as indicated in scheme (I) forming a new Si—C single bond and yielding a silicon containing component (iii):

scheme (I)

$$\underset{(i)}{\overset{1R}{\underset{3R}{\overset{|}{\underset{|}{2R^{\prime\prime\prime}}}}}\mathrm{Si}-\mathrm{H}} + \underset{(ii)}{\diagdown\diagup_{4R}} \xrightarrow{[\text{catalyst}]} \underset{(iii)}{\overset{1R}{\underset{3R}{\overset{|}{\underset{|}{2R^{\prime\prime\prime}}}}}\mathrm{Si}\diagdown\diagup_{4R}}$$

wherein $R_1$, $R_2$, $R_3$, $R_4$=(cyclo)aliphatic or aromatic or (cyclo)aliphatic aromatic or aromatic (cyclo)aliphatic moiety, wherein C and/or H atoms can also be substituted by e.g. O, Br, Cl, and Si atoms and that can also contain functionalities like (meth)acrylate groups.

That is, the carbosilane compound (A) of the present invention can be obtained via a hydrosilylation reaction according to general scheme (I) by reacting a poly SiH functional carbosilane component (i) with an olefinic substituted (meth)acrylate moiety containing component (ii) using e.g. common noble metal compounds as catalyst as described e.g. for similar siloxane based compounds in WO 01/92271 (preparation examples 1-5 on pages 23-25) resp. in U.S. Pat. No. 2003/0166816 (preparation examples 1-5 on pages 8-9) or in WO 00/38619 (example on page 26) resp. U.S. Pat. No. 6,566,413 (preparation example in column 22).

Poly SiH functional carbosilane components (i) like e.g. 1,3,5-Tris(dimethylsilyl)benzene and 2,4,6-Tris(dimethylsilyl)anisole can be synthesized via an in situ Grignard reaction as e.g. described by Beck, H., N., Chaffee, R., G., J. Chem. Eng. Data 1963, 8(3), 453-454.

Olefinic substituted (meth)acrylate moiety containing components (ii) like e.g. 5-vinyl-2(3)-norbornanyl-methacrylate can be synthesized via an addition reaction as e.g. described in U.S. Pat. No. 3,927,116 or are commercially available as e.g. (2-Allyloxyethyl)methacrylate.

Carbosilane containing component (A) of the inventive composition comprises preferably the following structural elements:

Si-Aryl bonds: at least 1, 2, 3 or 4 silicon atoms: at least 1, 2, 3, 4, 5 or 6, preferably 2 to 4 unsaturated moieties: at least 1, 2, 3, 4, 5, 6, preferably 2 to 4

Si-Oxygen bonds: none aromatic moieties: at least 1, 2, 3 or 4 optionally bicyclic moieties optionally a bisphenol derived spacer moiety.

Carbosilane containing component (A) can be as low as about 1 wt.-%, preferably as low as about 3 wt.-%, and more preferably as low as about 10 wt.-% with respect to the cured composition The amount of carbosilane containing component (A) can be as high as about 90 wt.-%, preferably as high as about 65 wt.-%, and more preferably as high as about 30 wt.-% with respect to the cured composition.

The amount of initiator (B) can be as low as about 0.01 wt.-%, preferably as low as about 0.1 wt.-%, and more preferably as low as about 0.5 wt.-% with respect to the cured composition.

The amount of initiator (B) can be as high as about 25 wt.-%, preferably as high as about 10 wt.-%, more preferably as high as about 3 wt.-% with respect to the cured composition.

The amount of filler (C) can be as low as about 3 wt.-%, preferably as low as about 25 wt.-%, more preferably as low as about 50 wt.-% with respect to the cured composition.

The amount of filler (C) can be as high as about 90 wt.-%, preferably as high as about 80 wt.-%, more preferably as high as about 75 wt.-% with respect to the cured composition.

The amount of optional component (D) can be as high as about 25 wt.-%, preferably as high as about 15 wt.-%, more preferably as high as about 3 wt.-% with respect to the cured composition.

The dental composition of the present invention meets preferably at least one of the following characteristics:

The viscosity of carbosilane containing component (A) usually can be equal or above about 0.1 Pa*s, equal or above about 1 Pa*s, equal or above about 2 Pa*s.

The viscosity of carbosilane containing component (A) usually does not exceed about 80 Pa*s, can be equal or below about 20 Pa*s or equal or below 5 about Pa*s.

The refractive index of carbosilane containing component (A) usually can be equal or above about 1.500, equal or above about 1.510, or equal or above about 1.520.

The refractive index usually does not exceed about 1.600, can be below about 1.580 or below about 1.560.

The opacity of the cured dental composition usually can be above about 10%, above about 40%, or above about 70%.

The opacity usually does not exceed about 92%, can be below about 90% or below about 88%.

The molecular mass (Mw) of carbosilane containing component (A) usually can be above about 500, above about 800, or above about 1200.

The molecular mass (Mw) usually does not exceed about 10.000, can be below about 5,000 or below about 2000.

The compressive strength usually can be above about 150 MPa, above about 200 MPa, or above about 250 MPa.

The flexural strength usually can be above about 50 MPa, above about 65 MPa, or above about 80 MPa.

If not indicated otherwise, the measurements were done at standard temperature and pressure ("STP", i.e. 23° C. and 1023 hPa) according to the methods described below.

The refractive index of carbosilane containing component (A) can be measured with a Kruess AR 4 D device (refractometer according to Abbe's measure principle). The refractive index is measured at 20.0° C. The refractive index is measured at a wavelength of 589 nm.

The viscosity of carbosilane containing component (A) can be measured with a Haake RotoVisco RV1 device (rotor C60/1 for viscosities up to 8000 mPa*s or rotor C20/1 for viscosities above 8000 mPa*s together with stator P61). The viscosity is measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94} for the viscosity measurement. Then the rotor is lifted and the material to be measured is put on the stator (1.0 ml with rotor C60/1 or 0.04 ml with rotor C20/1). Without undue delay, the rotor is lowered back to the preliminary adjusted measuring position. The material to be measured is tempered at 23.0° C. The shear rate for the measurement is adjusted to a value that produced a torque of at least 5000 μNm (therefore normally shear rates of 100, 200, 500, or 1000 s$^{-1}$ are used depending on the viscosity of the material to be measured). The measurement is started and run for 60s. The viscosity values (Pa*s) are recorded 20 s after the start of measurement and the mean value of the recorded values is given as viscosity.

The molecular weight ($M_w$) of carbosilane containing component (A) can be determined with GPC. Appropriate methods are know by the expert. In addition the determination of the molecular weight is possible using nuclear magnetic resonance spectroscopy (end-group determination).

The opacity of the cured dental composition can be measured by means of specimens with a defined height of 3.6 (+/−0.1) mm and a diameter of 20 (+/−0.1) mm. These are prepared by filling the material to be measured into suitably high rings, evenly and free of bubbles, and illuminating it in overlapping areas and in the contact every 40s by means of a lighting device (Trilight®, 3M ESPE) between plane, transparent, silicone oil treated glass slides. The opacity is then measured with the colour measuring device "HunterLab LabScan Spectralcolorimeter" of Hunter Lab Associates Laboratory, Inc., USA (Software SpecWare Software Version 1.01) and given by the device in %-values.

The compressive strength and the flexural strength can be measured comparably to ISO 9917, respectively according to ISO 4049. For the measurement of the compressive strength 10 specimens (3×3×5 mm) of each material are prepared according to the manufacturer's recommendations and the measurements are carried out comparably to ISO 9917 using an universal testing machine (Zwick Z 010, crosshead speed 4 mm/min). The compressive strength is given in MPa. The measurement of the flexural strength is carried out according to ISO 4049 using an universal testing machine (Zwick Z 010, crosshead speed 2 mm/min). The flexural strength is given in MPa.

Carbosilane containing component (A) of the inventive composition can be represented by formula (A):

with independently selected from each other
A=aliphatic or cycloaliphatic moiety (e.g. $C_1$ to $C_6$, methyl, ethyl, propyl, butyl, pentyl or hexyl, preferably $C_1$) or aromatic moiety (e.g. $C_6$ to $C_{14}$, phenyl, naphthyl, alkoxyphenyl, alkoxy naphthyl, preferably phenyl)
B=(meth)acrylate moiety (preferably methacrylate) attached onto spacer D
D=spacer=aliphatic or cycloaliphatic moiety (alkadiyl with $C_2$ to $C_{10}$, preferably $C_6$ and $C_9$), wherein C and/or H atoms can be substituted by O, Br, Cl, and Si atoms and which can comprise a bicyclic structural element as described in the text below
Br=bromine atom
C=carbon atom
Cl=chlorine atom
H=hydrogen atom
O=oxygen atom
Si=silicon atom
Aryl=aromatic moiety (e.g. $C_6$ to $C_{14}$, phenyl, naphthyl, alkoxyphenyl, alkoxy naphthyl, bisphenol A ethers or bisphenol F ethers, preferably phenyl)
a+b=3
a=0, 1 or 2 (preferably 2)
b=1, 2 or 3 (preferably 1)
n=1, 2, 3, 4, 5 or 6 (preferably 2 to 4)

Carbosilane containing component (A) of the inventive composition has usually a comparably high refractive index together with a comparably low viscosity. Carbosilane containing component (A) might also have in addition a comparably high molecular weight. Carbosilane containing component (A) may also have a comparably high lipophilicity.

Without wishing to be limited to any particular mechanism, it is thought that due to the aromatic moiety within carbosilane containing component (A) the refractive index and possibly also the lipophilicity are comparably high which might be of some importance for dental materials to achieve appropriate esthetics as well as to avoid staining and/or swelling by uptake of water and/or water soluble dyes (e.g. from coffee, tea, red wine).

Depending on the chemical structure of spacer D used or the chemical structures of a mixture of different types of spacers D used, a comparably low viscosity of carbosilane containing component (A) can be adjusted which might be of some importance for dental materials to achieve appropriate handling properties.

Moreover, without wishing to be limited to any particular mechanism, it is thought that due to of the comparably high molecular weight of carbosilane containing component (A) and/or different reactivities of (meth)acrylate moieties used within carbosilane compound (A), the volume shrinkage of derived dental compositions is reduced in comparison to conventional (meth)acrylate composites.

Spacer D can be a mixture of different types of spacers having a similar and/or non similar chemical structure within the same molecule. The use of a mixture of different types of spacers D within the same molecule is of special interest concerning to the tailor-made adjustment of viscosity and/or reactivity and/or polarity and/or refractive index of the carbosilane containing component (A) as well as of the properties of the cured dental composition like stiffness.

In preferred embodiments carbosilane containing component (A) can be characterized by formulas (I-IV) depending on the molecular structure of carbosilane containing component (A) as well as on the number m of the structural elements $\{Aryl-[Si(A)_a(D-B)_b]_n\}_m$ within carbosilane containing component (A).

In a preferred embodiment carbosilane containing component (A) comprises only one aromatic moiety within the molecule in the structural element $\{Aryl-[Si(A)_a(D-B)_b]_n\}_m$ (i.e. m=1) as well as only one Aryl-Si bond (i.e. n=1) which can be characterized by formula (I), wherein the indices are as defined above:

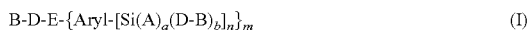

with independently selected from each other
m=1
n=1
E=(cyclo)aliphatic moiety (alkadiyl with $C_5$ to $C_{11}$, preferably $C_7$ and $C_9$), wherein at least one C atom may be substituted by a Si atom and wherein other C and/or H atoms can be substituted by O, Br, Cl, and Si atoms, wherein the indices are as defined above.

Preferred examples of carbosilane containing component (A) according to formula (I) are given below wherein B = 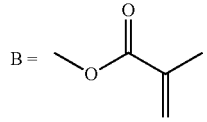

D = 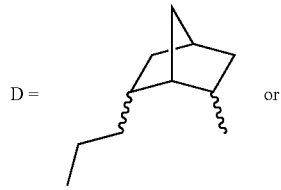 or

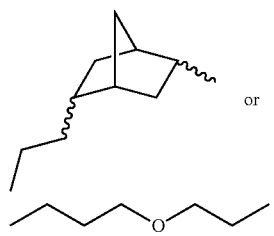 or

MA = (D - B) = 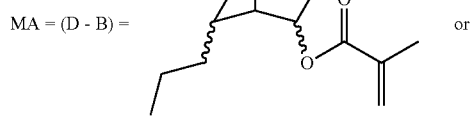 or

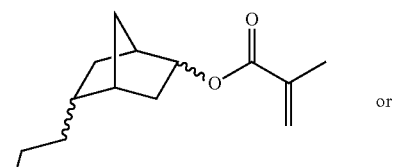 or

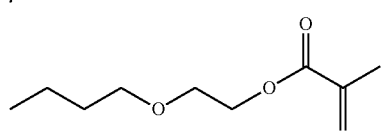

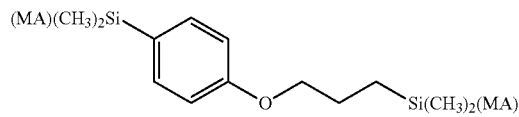

with: A=$C_1$, a=2, b=1, E=$C_7$ with C substituted in part by O and Si, Aryl=phenyl

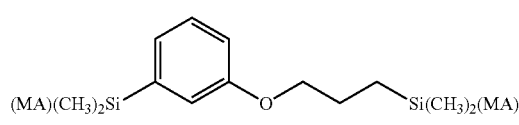

with: A=$C_1$, a=2, b=1, E=$C_7$ with C substituted in part by O and Si, Aryl=phenyl

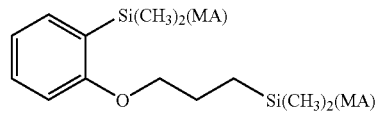

with: A=$C_1$, a=2, b=1, E=$C_7$ with C substituted in part by O and Si, Aryl=phenyl

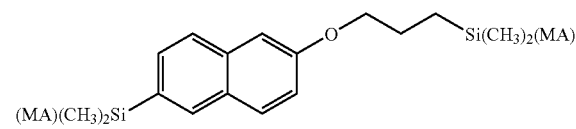

with: A=$C_1$, a=2, b=1, E=$C_7$ with C substituted in part by O and Si, Aryl=naphthyl

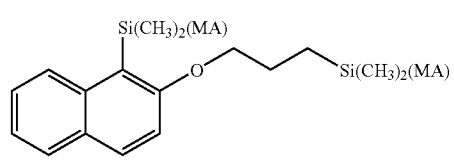

with: A=$C_1$, a=2, b=1, E=$C_7$ with C substituted in part by O and Si, Aryl=naphthyl The following compounds are examples of preferred poly SiH functional carbosilane components (i) which can be used according to scheme (I) for the synthesis of carbosilane containing component (A) fulfilling the requirements according to formula (I):

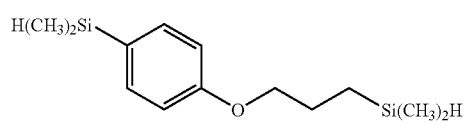

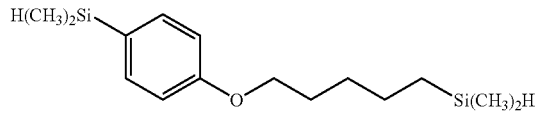

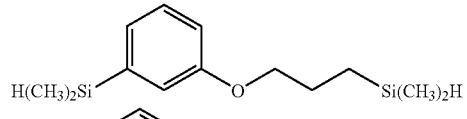

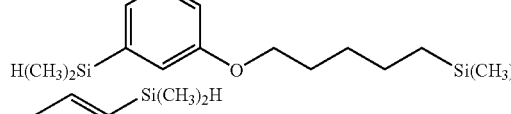

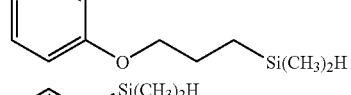

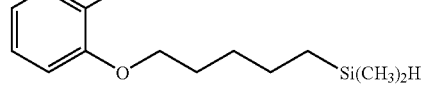

-continued

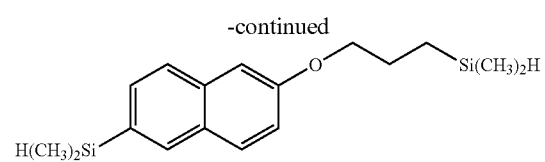

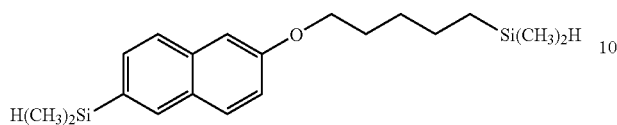

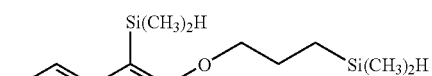

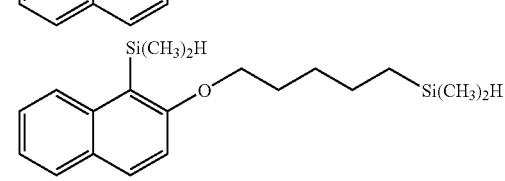

The following compounds are examples of preferred olefinic substituted (meth)acrylate moiety containing components (ii) which can be used according to scheme (I) for the synthesis of carbosilane containing component (A) fulfilling the requirements according to formula (I):

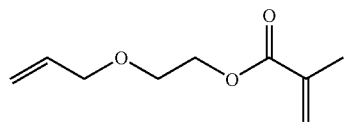

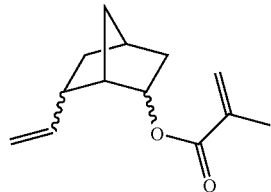

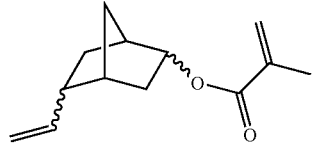

In a further preferred embodiment carbosilane containing component (A) comprises only one aromatic moiety within the molecule in the structural element {Aryl-[Si(A)$_a$(D-B)$_b$]$_n$}$_m$ (i.e. m=1) as well as more than one Aryl-Si bond (i.e. n≧2) and can be characterized by formula (II):

{Aryl-[Si(A)$_a$(D-B)$_b$]$_n$}$_m$      (II)

with independently selected from each other
m=1
n=2, 3, 4, 5 or 6 (preferably 2 to 4)
wherein the indices are as defined above.

Preferred examples of carbosilane containing component (A) according to formula (II) are given below:
wherein

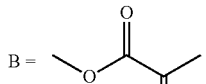

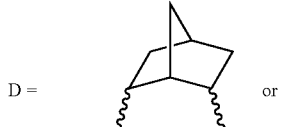

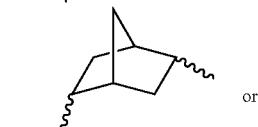

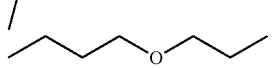

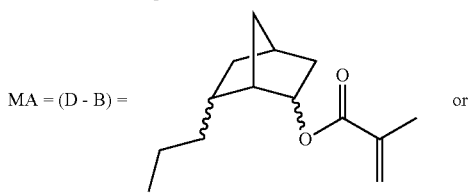

with: A=C$_1$, a=2, b=1, n=2, Aryl=phenyl

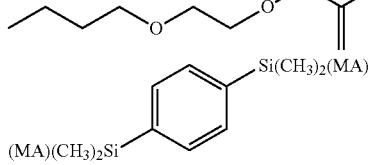

with: A=C$_1$, a=2, b=1, n=2, Aryl=phenyl

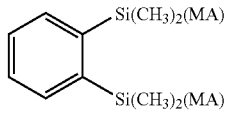

with: A=$C_1$, a=2, b=1, n=2, Aryl=phenyl

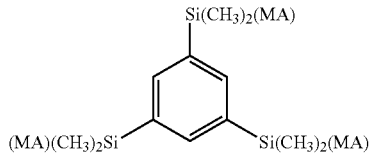

with: A=$C_1$, a=2, b=1, n=3, Aryl=phenyl

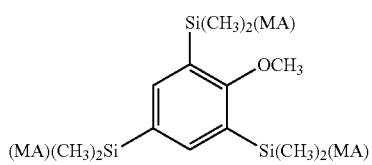

with: A=$C_1$, a=2, b=, n=3, Aryl=phenyl

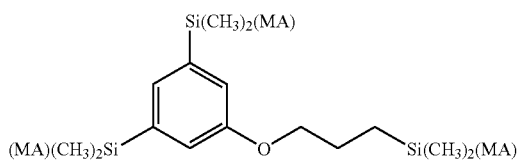

with: A=$C_1$, a=2, b=1, n=2, Aryl=phenyl

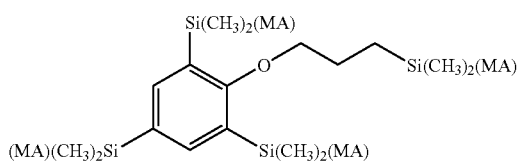

with: A=$C_1$, a=2, b=1, n=3, Aryl=phenyl

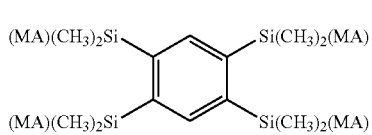

with: A=$C_1$, a=2, b=1, n=4, Aryl=phenyl

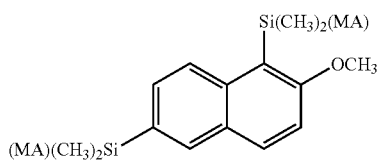

with: A=$C_1$, a=2, b=1, n=2, Aryl=naphthyl

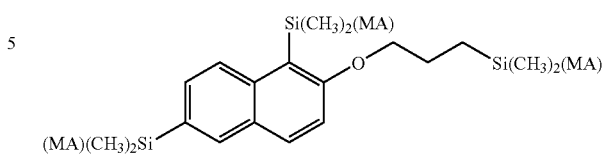

with: A=$C_1$, a=2, b=1, n=2, Aryl=naphthyl

The following compounds are examples of preferred poly SiH functional carbosilane components (i) used according to scheme (I) for the synthesis of carbosilane containing component (A) fulfilling the requirements according to formula (II):

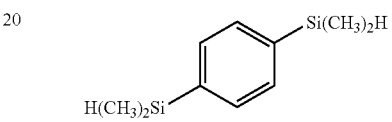

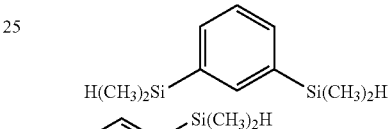

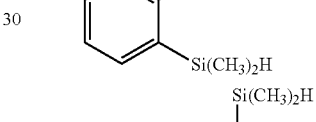

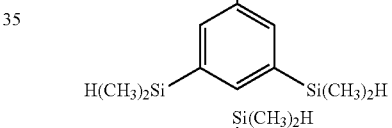

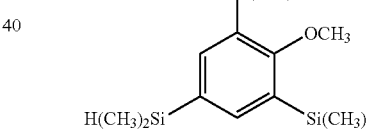

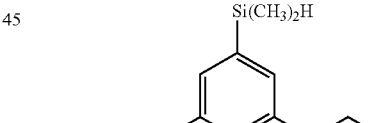

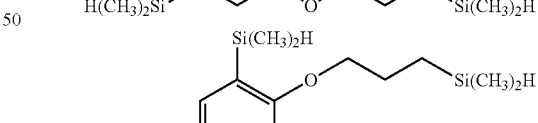

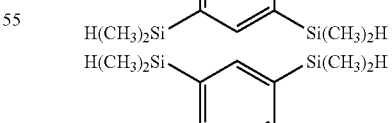

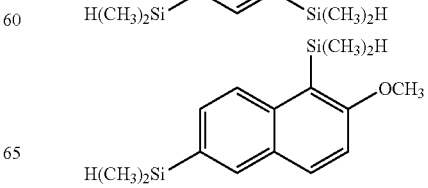

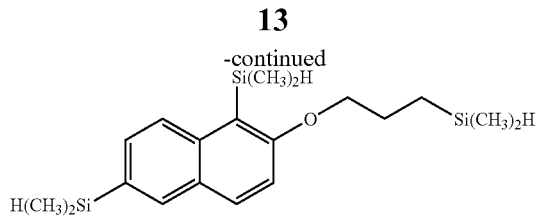

The following compounds are examples of preferred olefinic substituted (meth)acrylate moiety containing components (ii) used according to scheme (I) for the synthesis of carbosilane containing component (A) fulfilling the requirements according to formula (II):

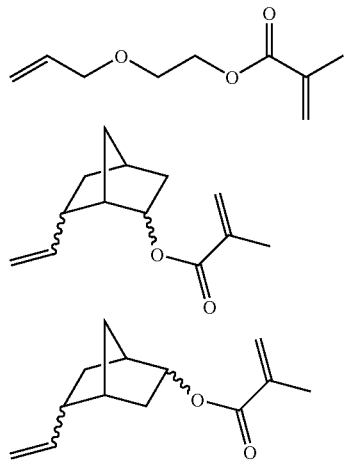

In a further preferred embodiment carbosilane containing component (A) comprises more than one aromatic moiety within the molecule in the structural element {Aryl-[Si(A)$_a$(D-B)$_b$]$_n$}$_m$ (i.e. m>2) and can be characterized by formula (III):

$$F\text{-}\{Aryl\text{-}[Si(A)_a(D\text{-}B)_b]_n\}_m \quad (III)$$

with independently selected from each other
m=2, 3 or 4 (preferably 2)
n=1, 2, 3, 4, 5 or 6 (preferably 2)
F=(cyclo)aliphatic moiety (alkadiyl with $C_0$ to $C_{25}$, preferably $C_0$ to $C_9$) wherein C and/or H atoms can be substituted by O, Br, Cl, and Si atoms (e.g. F can be O)
wherein the indices are as defined above.

Preferred examples of carbosilane containing component (A) according to formula (III) are given below, wherein

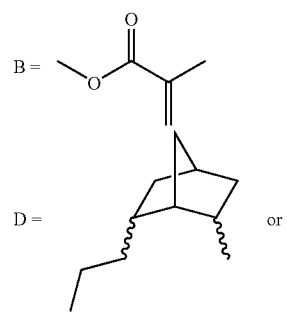

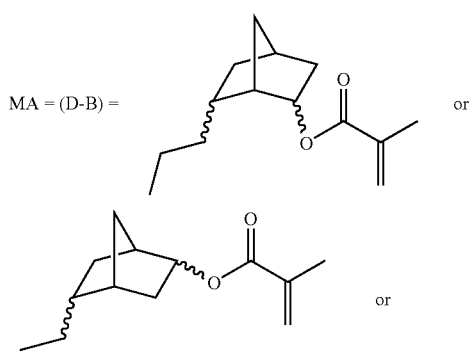

with: A=$C_1$, a=2, b=1, m=2, n=1, F=$C_1$ with C substituted by O, Aryl=phenyl

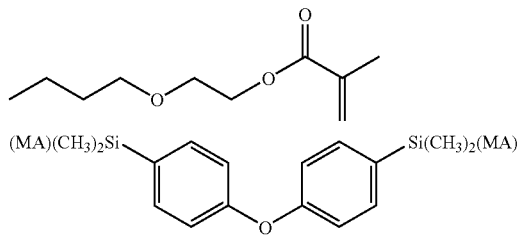

with: A=$C_1$, a=2, b=1 m=2, n=1, F=$C_1$, Aryl=phenyl

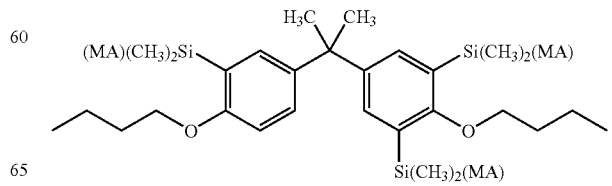

15
with: A=C$_1$, a=2, b=1, m=2, n=1, F=C$_3$, Aryl=phenyl
16
with: A=C$_1$, a=2, b=1, m=2, n=2, F=C$_3$, Aryl=phenyl
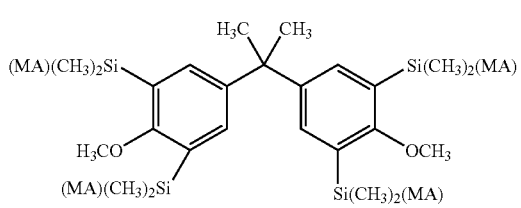
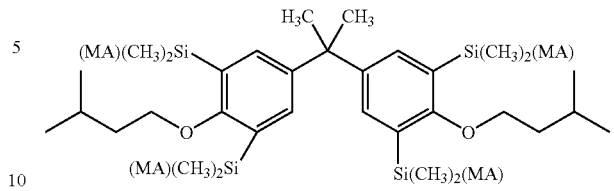
with: A=C$_1$, a=2, b=1, m=2, n=2, F=C$_3$, Aryl=phenyl
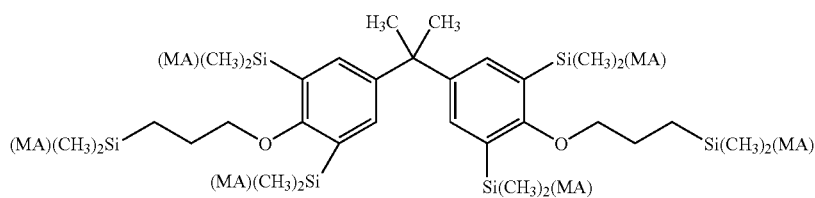
with: A=C$_1$, a=2, b=1, m=2, n=2, F=C$_3$, Aryl=phenyl
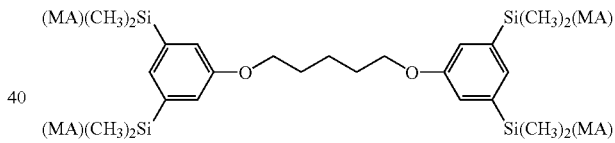
with: A=C$_1$, a=2, b=1, m=2, n=2, F=C$_7$ with C substituted in part by O, Aryl=phenyl
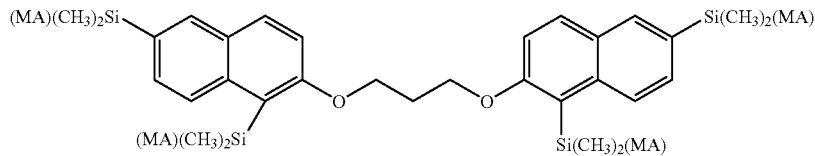

with: A=$C_1$, a=2, b=1, m=2, n=2, F=$C_5$ with C substituted in part by O, Aryl=naphthyl

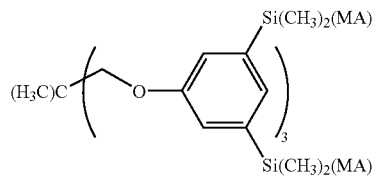

with: A=$C_1$, a=2, b=1, m=3, n=2, F=$C_8$ with C substituted in part by O, Aryl=phenyl

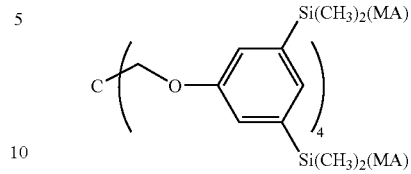

with: A=$C_1$, a=2, b=1, m=4, n=2, F=$C_9$ with C substituted in part by O, Aryl=phenyl The following compounds are examples of preferred poly SiH functional carbosilane components (i) used according to scheme (I) for the synthesis of carbosilane containing component (A) fulfilling the requirements according to formula (III):

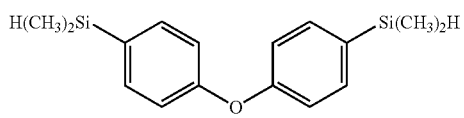

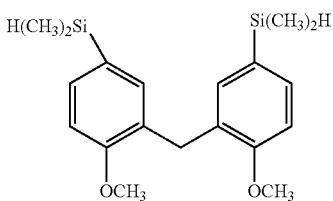

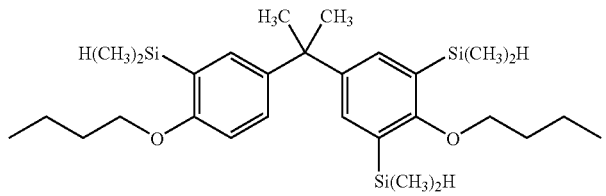

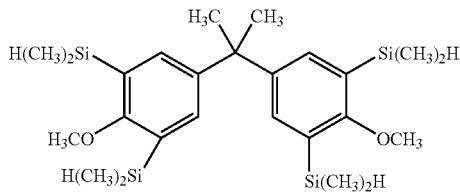

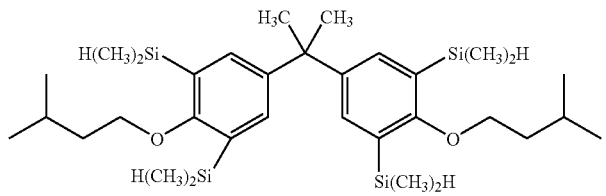

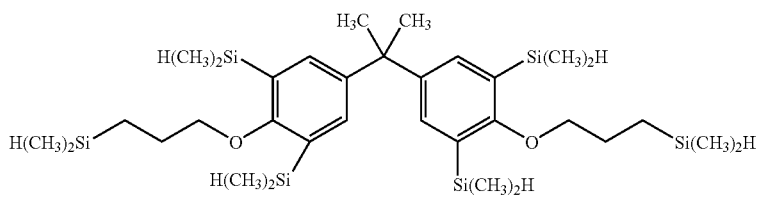

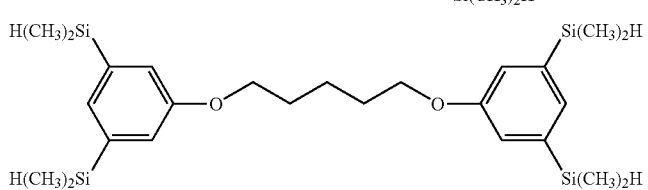

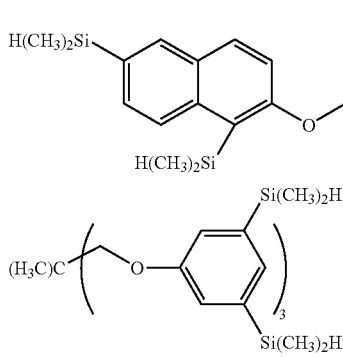
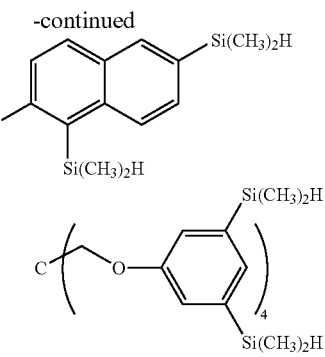

The following compounds are examples of preferred olefinic substituted (meth)acrylate moiety containing components (ii) used according to scheme (I) for the synthesis of carbosilane containing component (A) fulfilling the requirements according to formula (III):

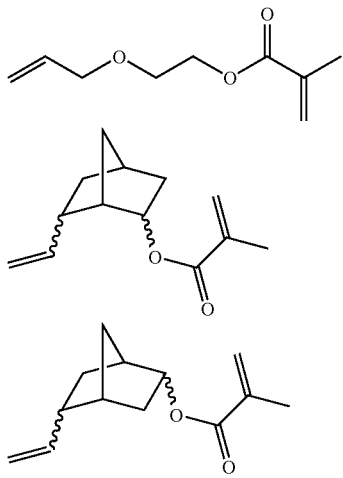

In another preferred embodiment carbosilane containing component (A) comprises more than one aromatic moiety within the molecule not only in the structural element {Aryl-[Si(A)$_a$(D-B)$_b$]$_n$}$_m$ and can be characterized by formula (IV):

G-{Aryl-[Si(A)$_a$(D-B)$_b$]$_n$}$_m$     (IV)

with independently selected from each other
m=2, 3 or 4 (preferably 2)
n=1, 2, 3, 4, 5 or 6 (preferably 2 to 4)
G=(cyclo)aliphatic or aromatic or (cyclo)aliphatic aromatic or aromatic (cyclo)aliphatic moiety (diyl with $C_1$ to $C_{100}$, preferably $C_3$ to $C_{63}$), wherein C and/or H atoms can be substituted by O, Br, Cl, and Si atoms
wherein the indices are as defined above.

Preferred examples of carbosilane containing component (A) according to formula (IV) are given below, wherein

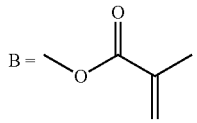

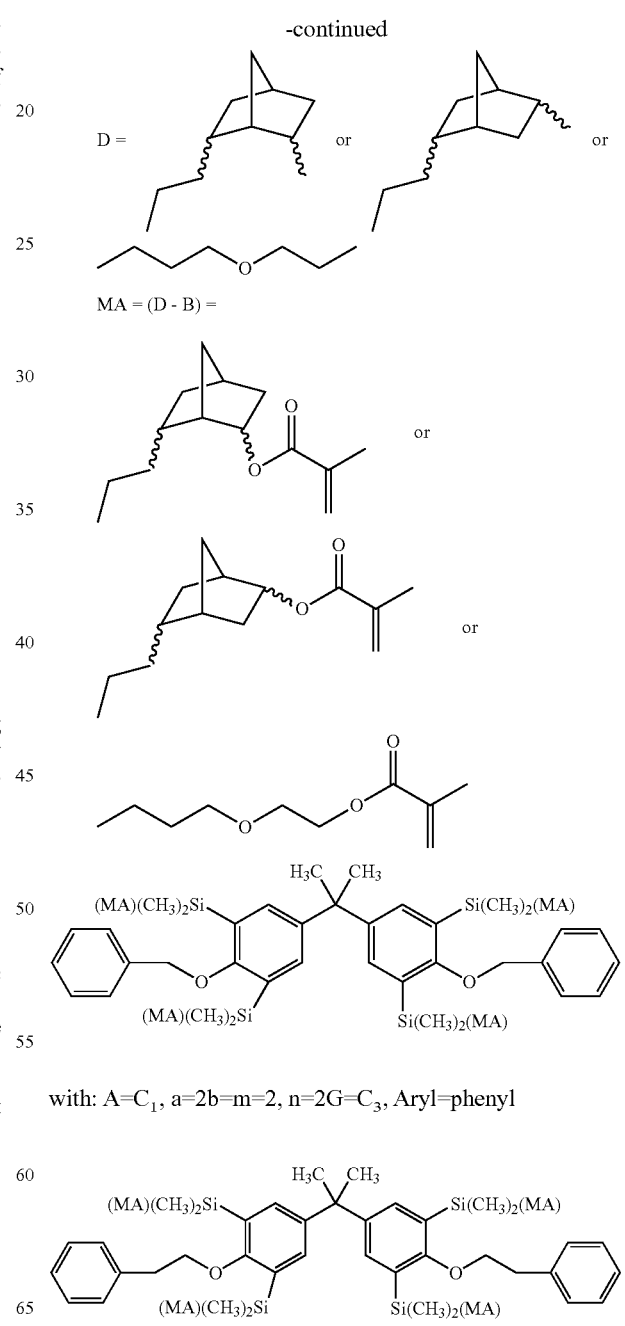

with: A=$C_1$, a=2b=m=2, n=2G=$C_3$, Aryl=phenyl with: A=$C_1$, a=2, b=1, m=2, n=2, G=$C_3$, Aryl=phenyl

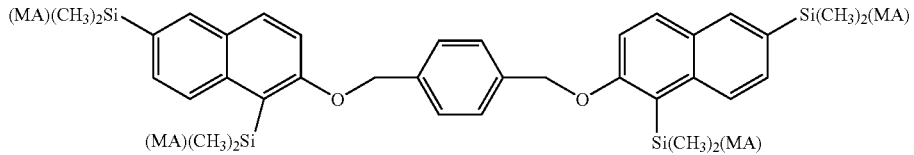

with: A=$C_1$, a=2, b=1, m=2, n=2, G=$C_{10}$ with C substituted in part by O, Aryl=naphthyl The following compounds are examples of preferred poly SiH functional carbosilane components (i) used according to scheme (I) for the synthesis of carbosilane containing component (A) fulfilling the requirements according to formula (IV):

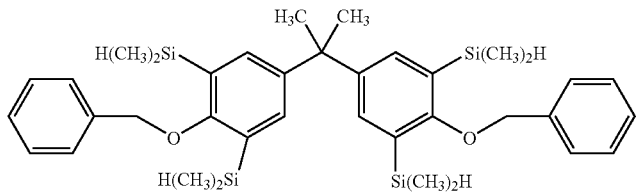

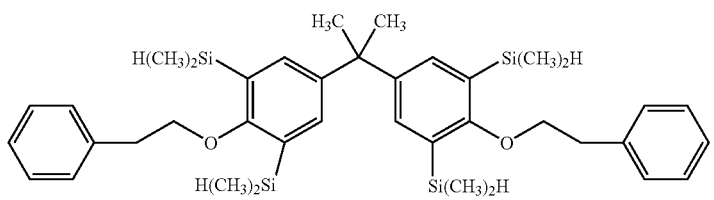

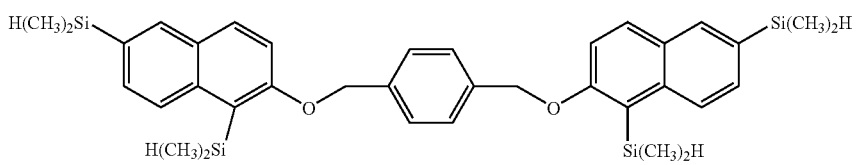

In a further preferred embodiment carbosilane containing component (A) according to formula (IV) can be represented by formula (IVa), wherein the indices are as defined above:

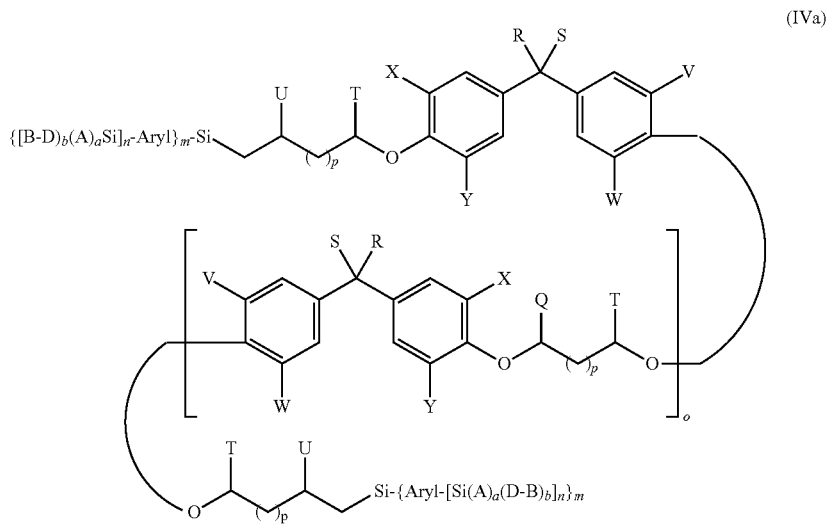
(IVa)

wherein
p=0, 1, 2, 3 or 4
o=0, 1, 2, 3, 4 or 5
Q=H or CH$_3$
R, S=H, CH$_3$, phenyl or C$_{5-9}$ alkadiyl (e.g. R+S=(CH$_2$)$_5$, CH$_2$—CH(CH$_3$)—CH$_2$—CH$_2$—CH$_2$, CH$_2$—CH$_2$—CH(CH$_3$)—CH$_2$—CH$_2$, CH$_2$—C(CH$_3$)$_2$—CH$_2$—CH(CH$_3$)—CH$_2$)

T, U=H or CH$_3$

V, W, X, Y=H, Br or Cl wherein the indices are as defined above.

Preferred examples of carbosilane containing component (A) according to formula (IVa) are given below:

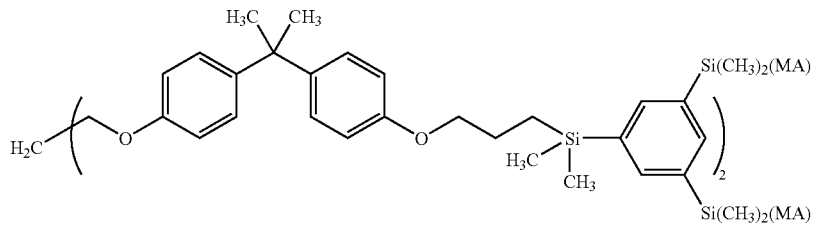

with: A=C$_1$, a=2, b=1, m=2, n=2, G=C$_{49}$ with C substituted in part by O and Si, Aryl=phenyl

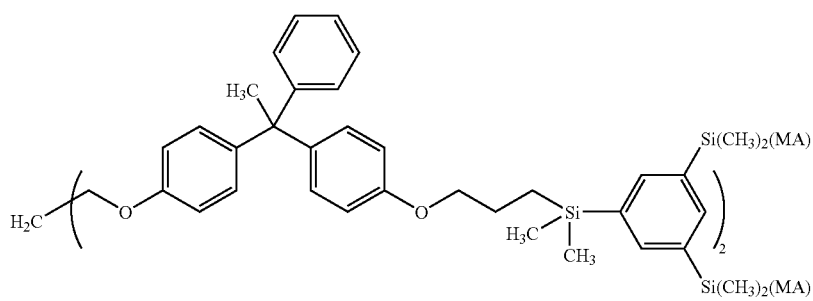

with: A=$C_1$, a=2, b=1, m=2, n=2, G=$C_{59}$ with C substituted in part by O and Si, Aryl=phenyl

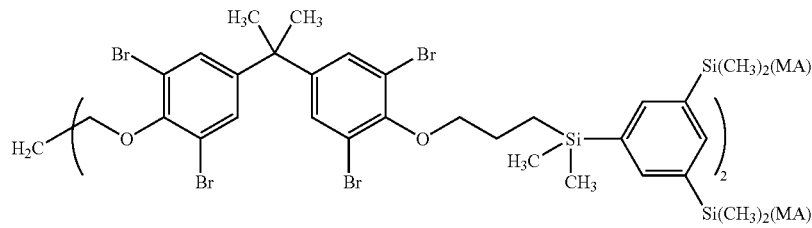

with:
A=$C_1$, a=2, b=1, m=2, n=2, G=$C_{57}$ with C substituted in part by Br, O, and Si, Aryl=phenyl

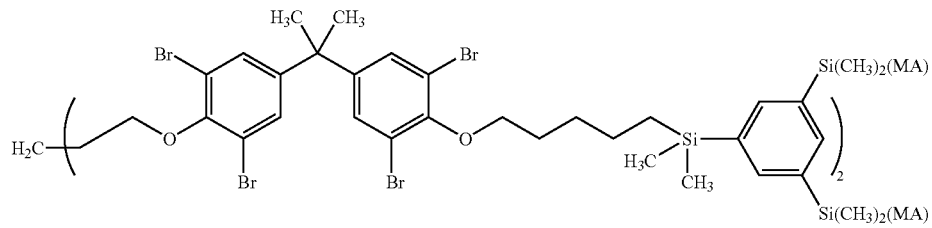

with: A=$C_1$, a=2, b=1, m=2, n=2, G=$C_{63}$ with C substituted in part by Br, O, and Si, Aryl=phenyl In another embodiment carbosilane containing component (A) according to formula (IVa), with o=0, can be represented by formula (IVb), wherein the indices are as defined above:

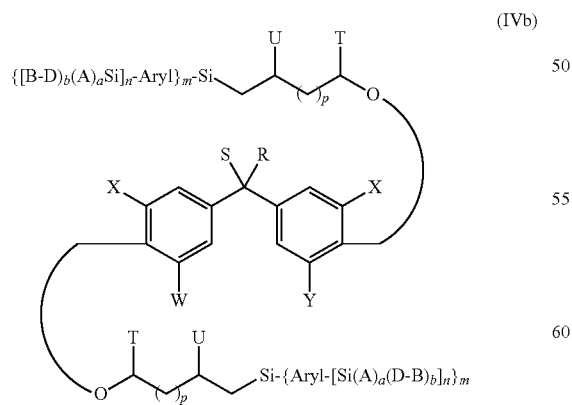

(IVb)

wherein the indices are as defined above.

Preferred examples of carbosilane containing component (A) according to formula (IVb) are given below:
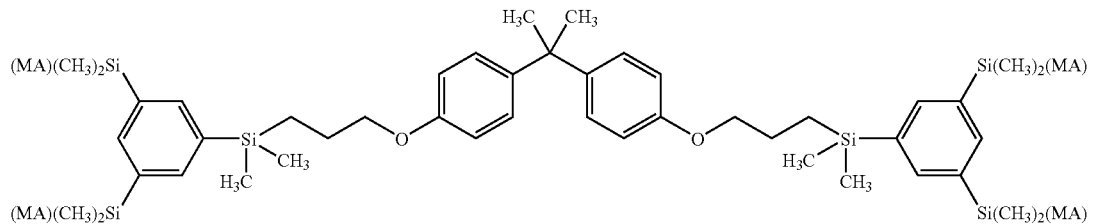
with: A=C$_1$, a 2, b=1, m=2, n=2, G=C$_{29}$ with C substituted in part by O and Si, Aryl=phenyl
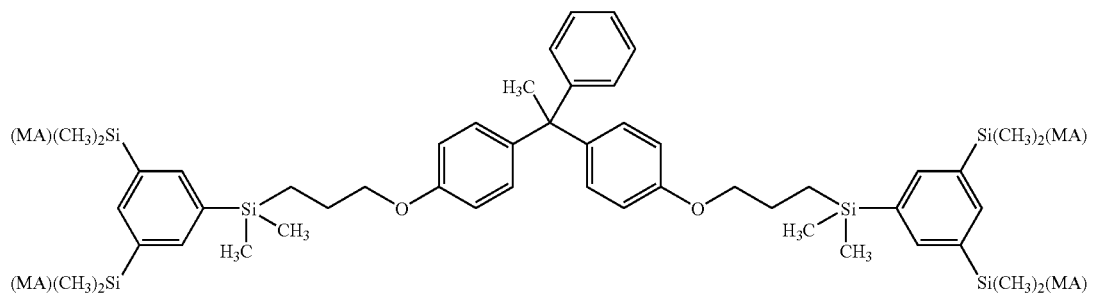
with: A=C$_1$, a=2, b=1, m=2, n=2, G=C$_{34}$ with C substituted in part by O and Si, Aryl=phenyl
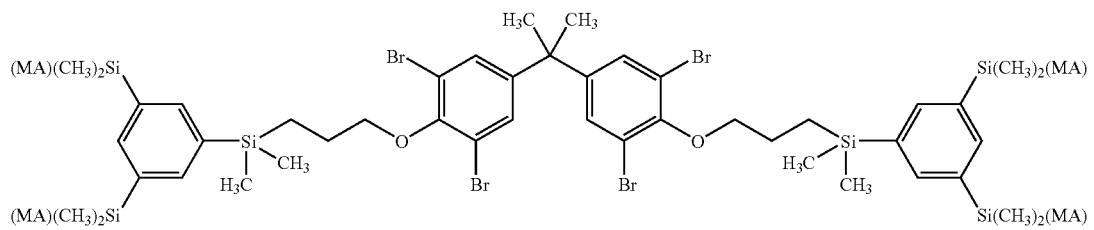
with: A=C$_1$, a=2, b=1, m=2, n=2, G=C$_{33}$ with C substituted in part by Br, O, and Si, Aryl=phenyl
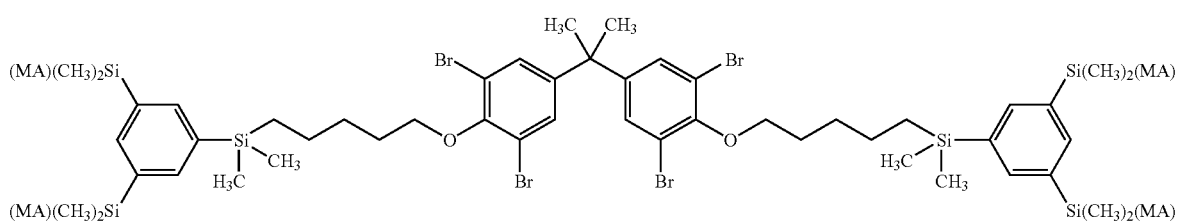

with: A=$C_1$, a=2, b=1, m=2, n=2, G=$C_{37}$ with C substituted in part by Br, O, and Si, Aryl=phenyl
The following compounds are examples of preferred poly SiH functional carbosilane components (i) used according to scheme (I) for the synthesis of carbosilane containing component (A) fulfilling the requirements according to formulas (IVa), and (IVb):
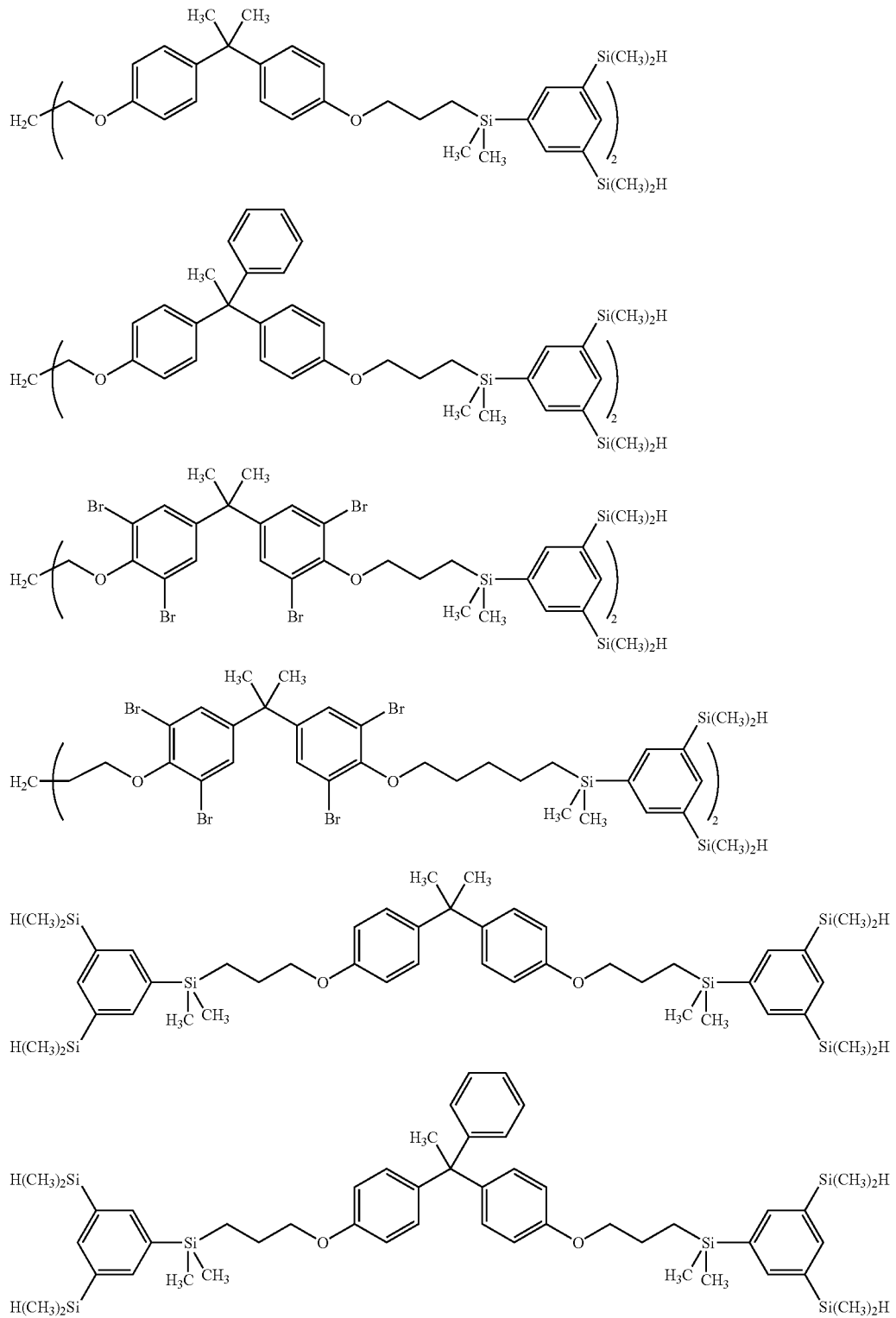

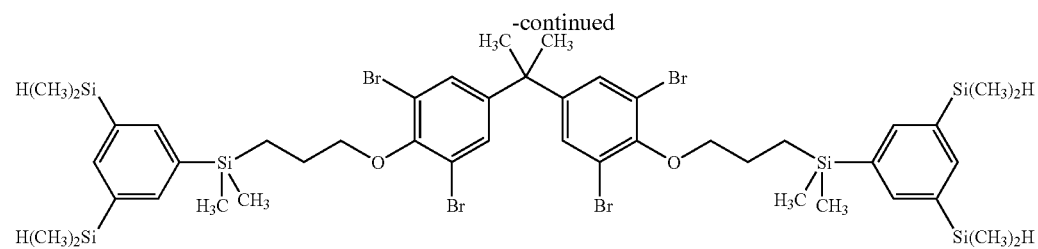
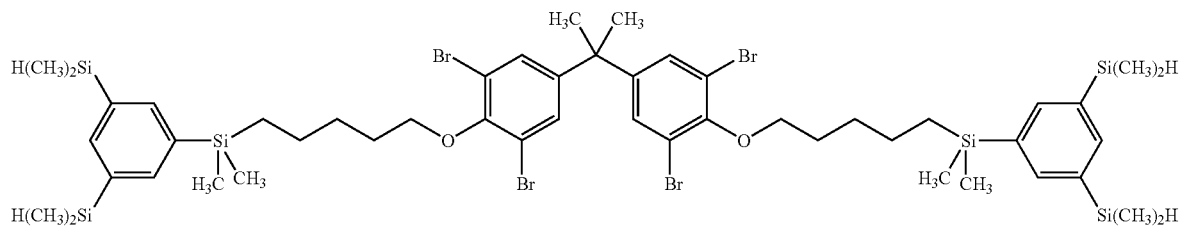
These poly SiH functional carbosilane components (i) can be synthesized e.g. via hydrosilation reaction of non silicon containing diolefinic precursor (ia) and poly SiH functional carbosilane component (ib) used according to scheme (I) for the synthesis of SiH compound (i).
Preferred examples of non silicon containing diolefinic precursors (ia) are:
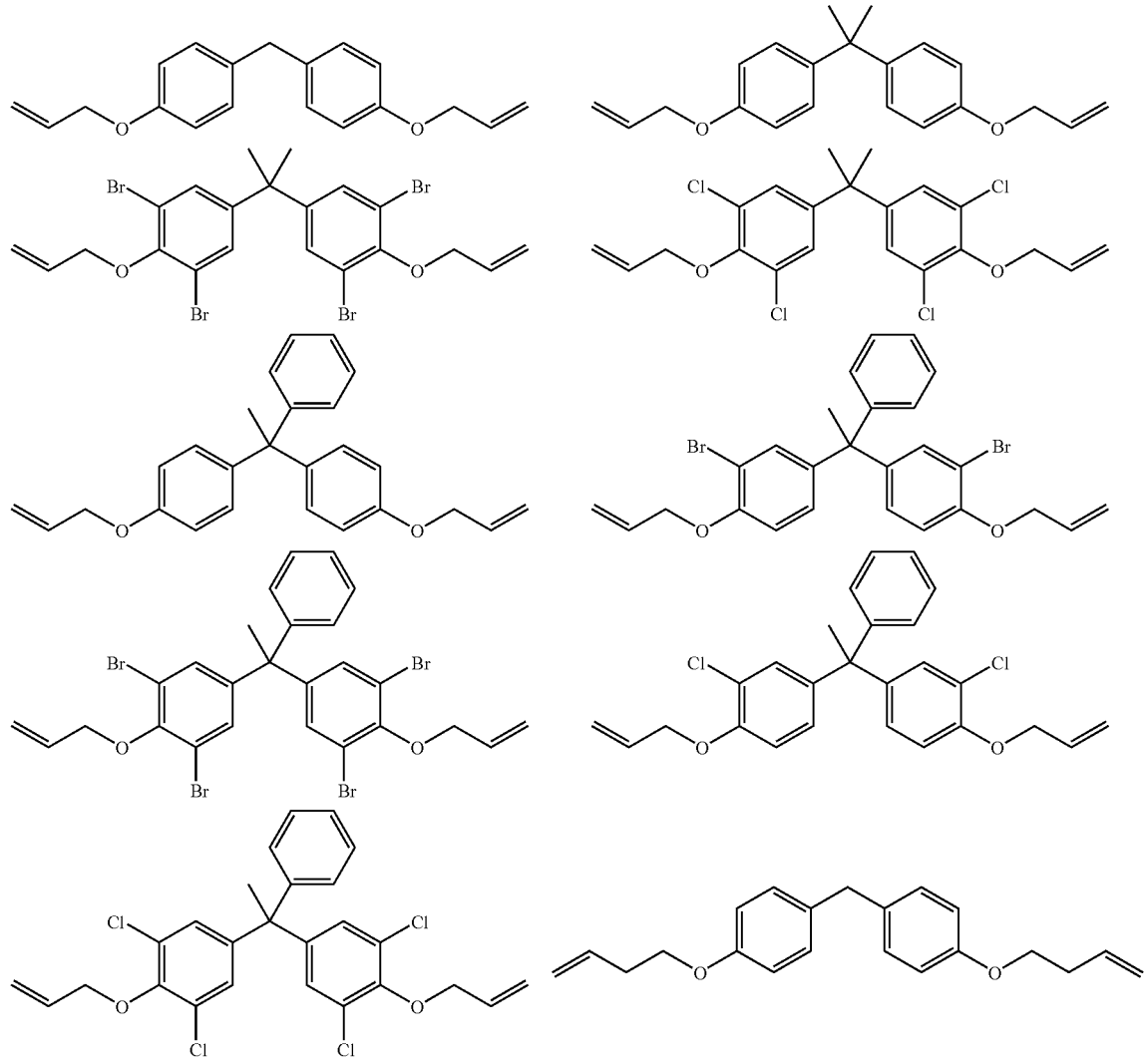

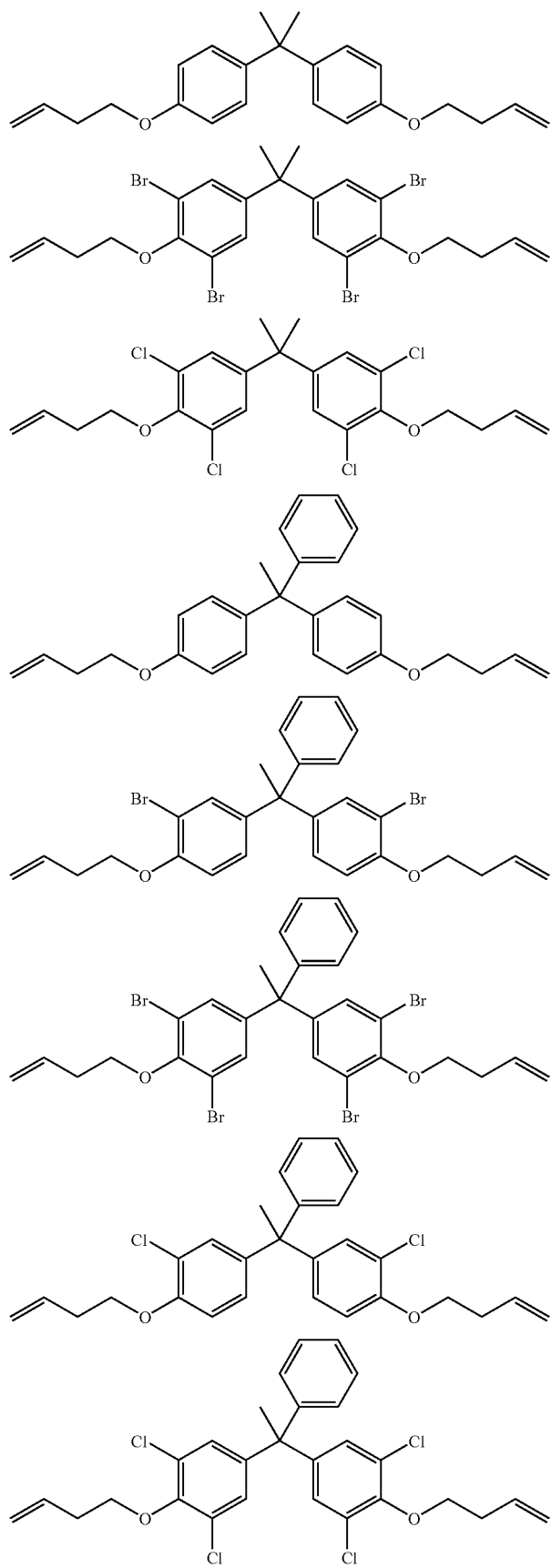

-continued
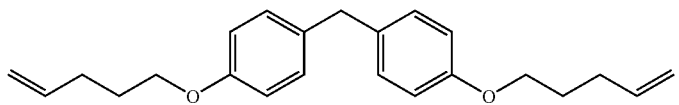
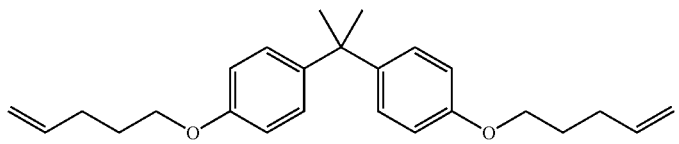
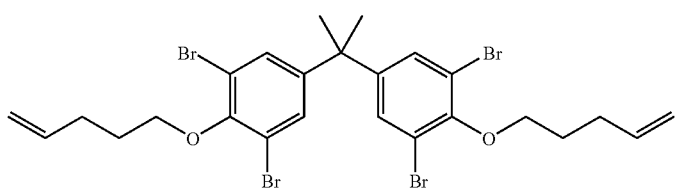
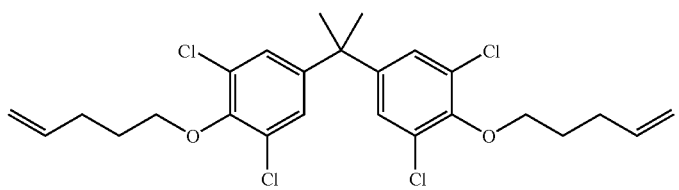
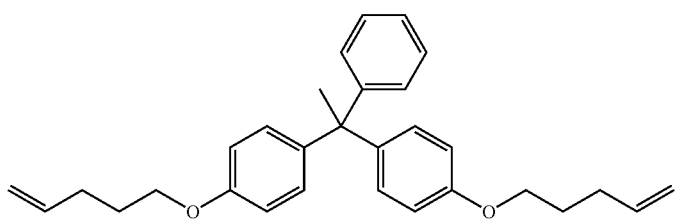
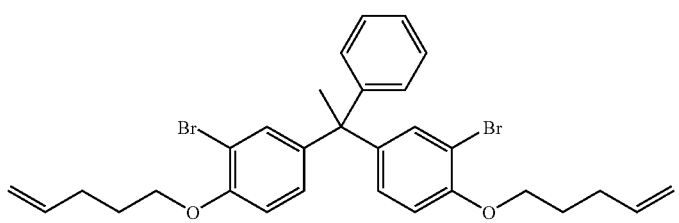
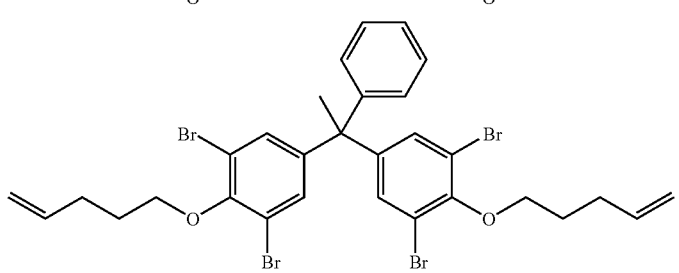
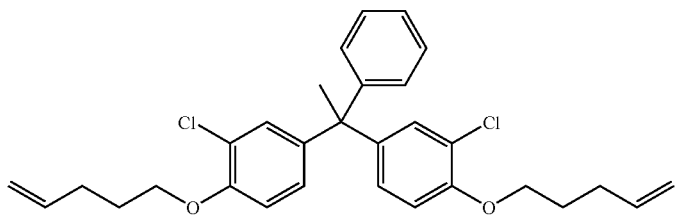

-continued
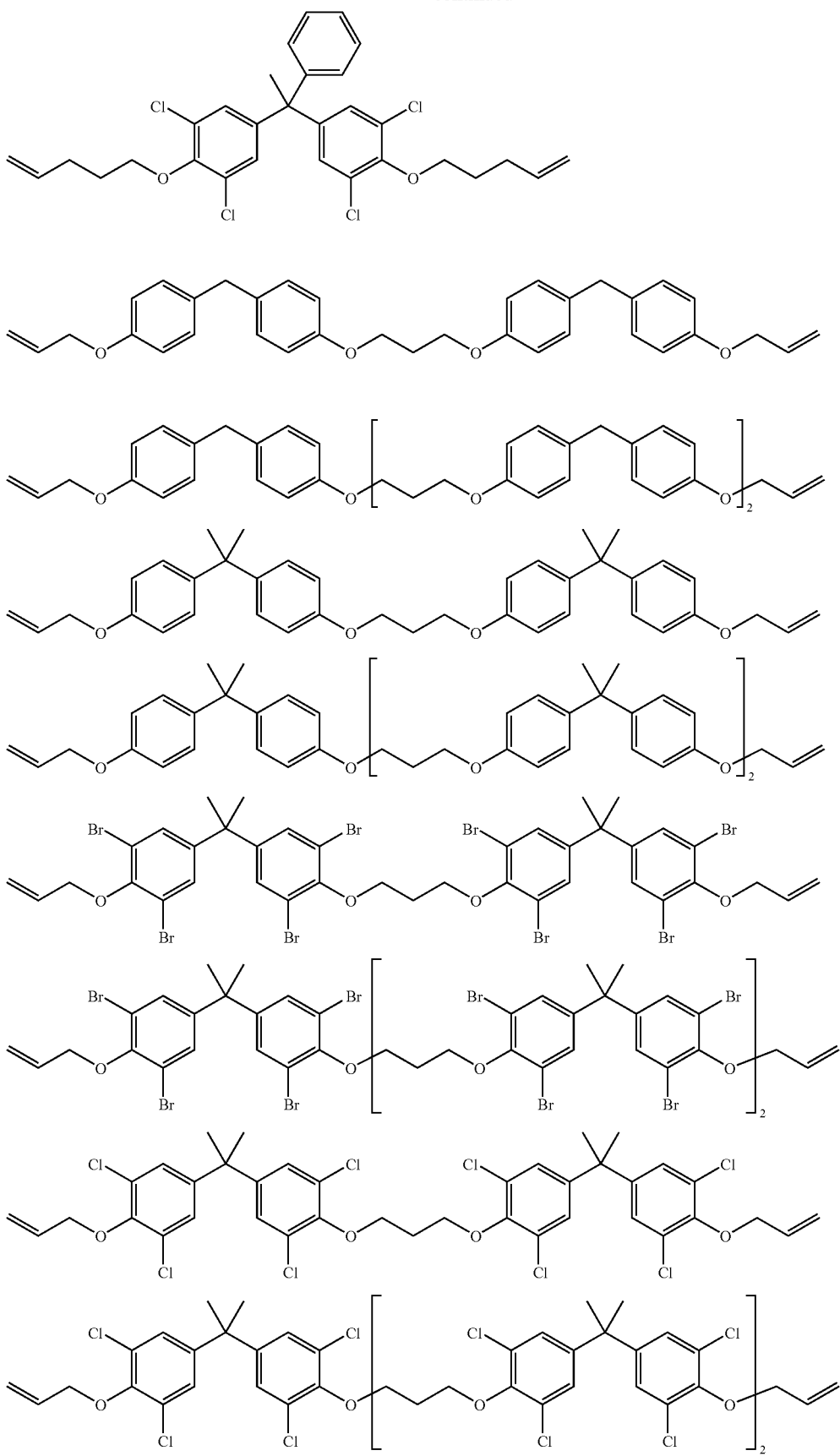

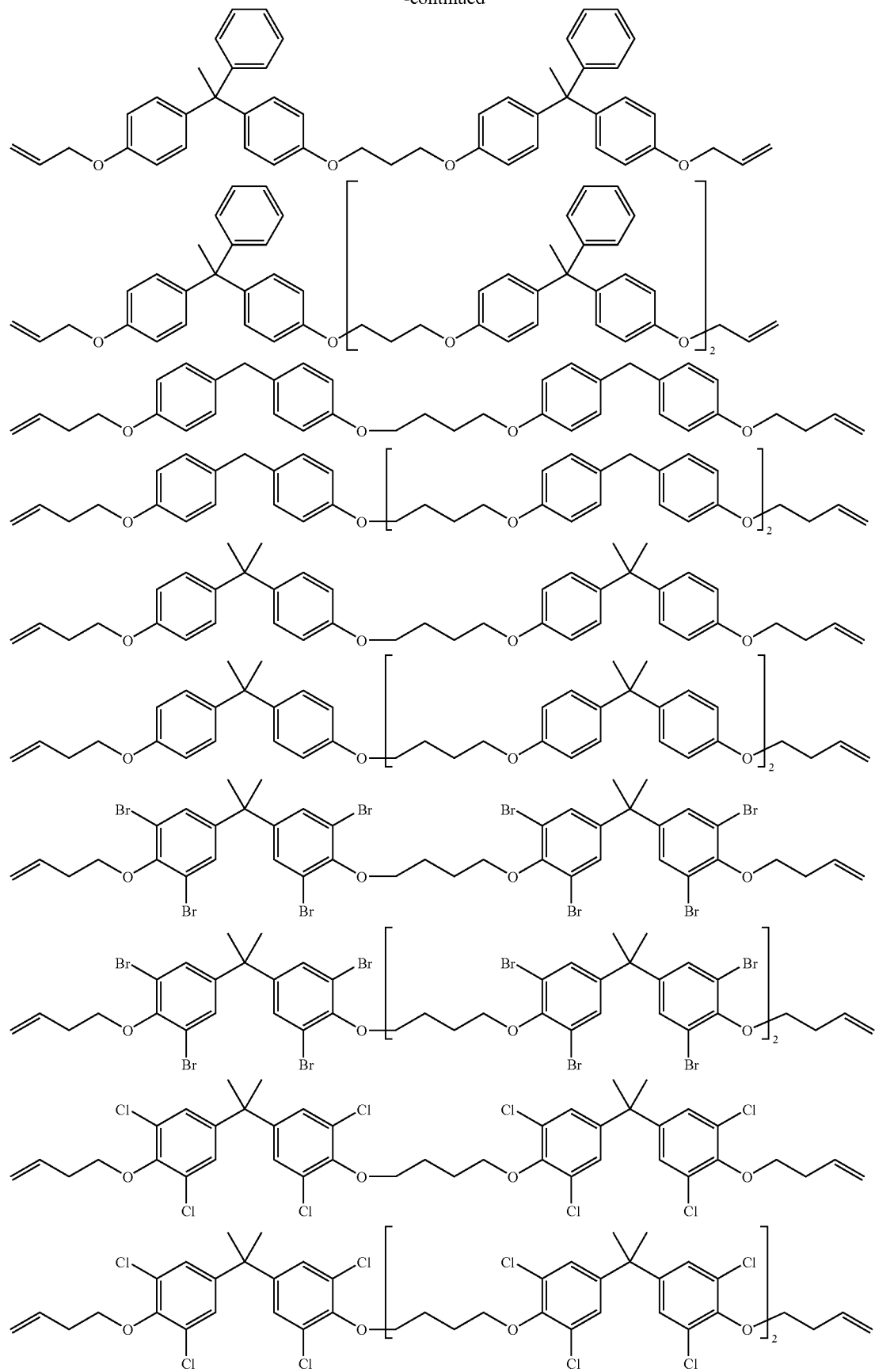

-continued
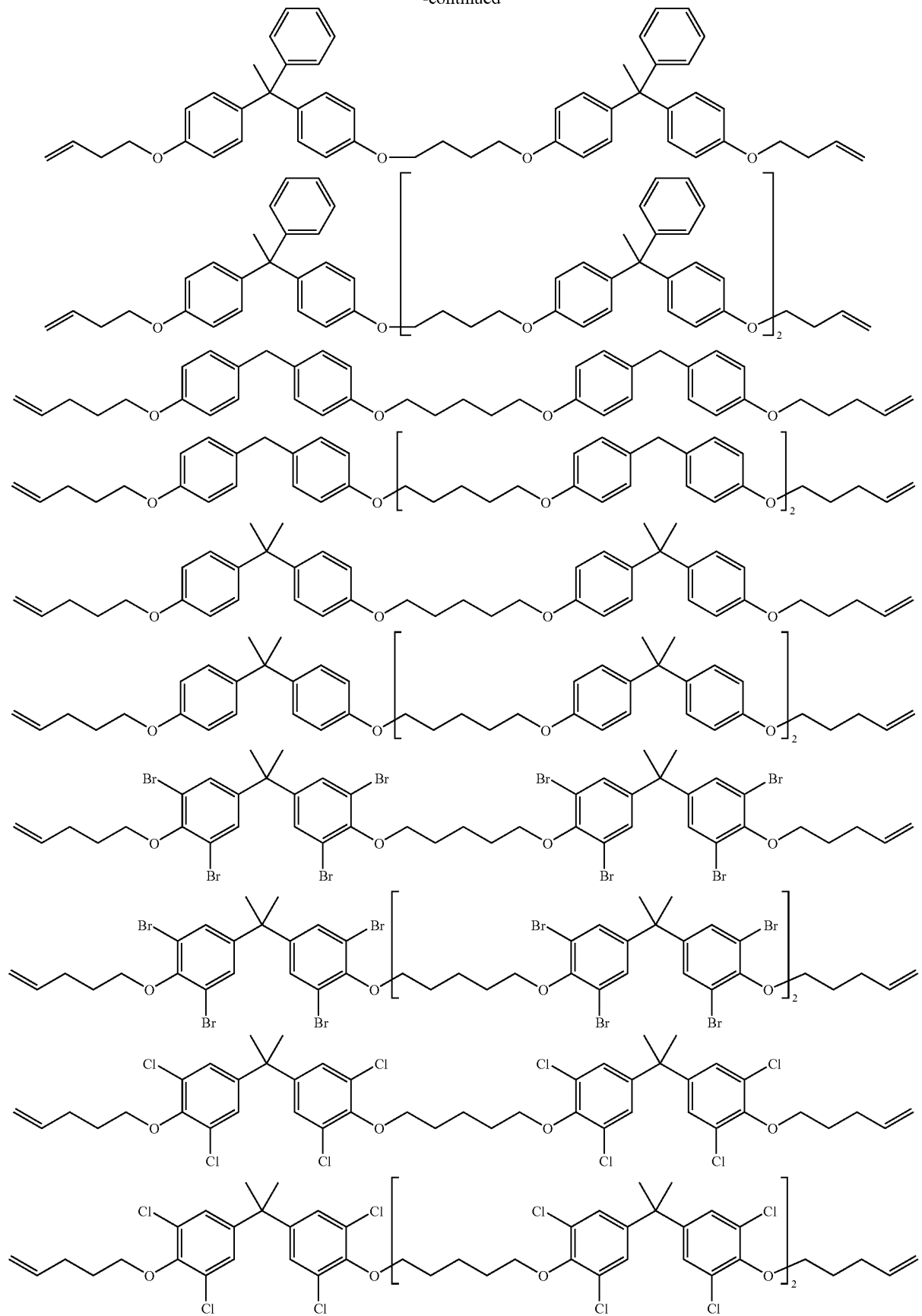

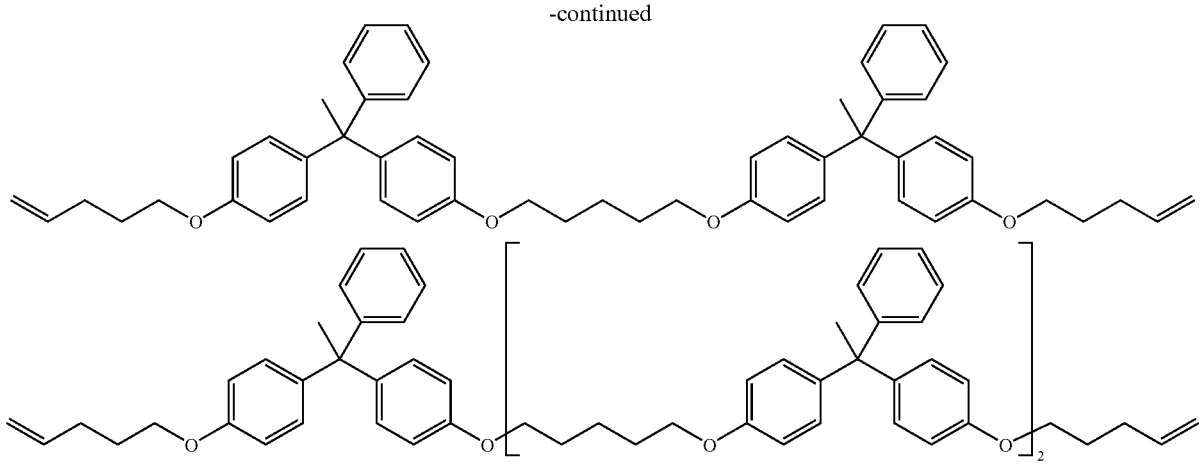

Examples of preferred poly SiH functional carbosilane components (ib) are:

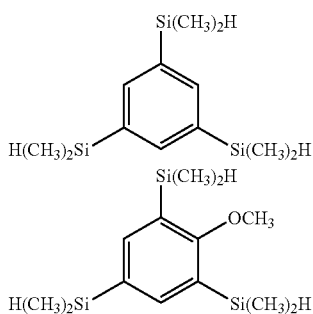

The following compounds are examples of preferred olefinic substituted (meth)acrylate moiety containing components (ii) used according to scheme (I) for the synthesis of carbosilane containing component (A) fulfilling the requirements according to formulas (IV), (IVa), and (IVb):

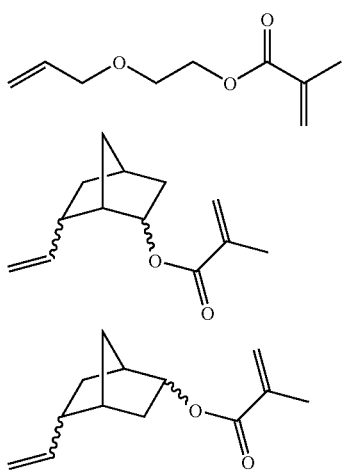

Useful initiators (B) can initiate curing of carbosilane compound (A) of the composition. Such initiators can be light curing or redox curing. Both types of initiators are well known to the skilled person in the art.

Examples of photoinitiators are benzoin alkyl ethers, benzil ketals, acylphosphinic oxides or aliphatic and aromatic 1,2-diketone compounds, for example camphorquinone, the light polymerization can be accelerated by the addition of activators, such as tertiary amines or organic phosphites.

Suitable initiator systems for the triggering of the polymerization via redox mechanism are e.g. the peroxide/amine and peroxide/barbituric acid derivatives systems.

When using such initiator systems, it is expedient to keep initiator (e.g. peroxide) and catalyst components (e.g. amine) separately. The two components are usually homogeneously mixed with each other shortly before they are used.

The composition of the present invention also includes a filler (C), preferably inorganic fillers like quartz, ground glasses, silica gels as well as pyrogenic silicic acids and precipitation silicic acids or their granules. X-ray-opaque fillers are also preferably used, at least partially. These can for example be X-ray-opaque glasses, i.e. glasses which for example contain strontium, barium or lanthanum (e.g. according to U.S. Pat. No. 3,971,754) or some of the fillers consist of an X-ray-opaque additive, such as for example yttrium trifluoride, strontium hexafluorozirconate or fluorides of the rare earth metals (e.g. according to EP 0 238 025 A1). For better incorporation into the polymer matrix, it is advantageous to hydrophobize the inorganic fillers. Customary hydrophobization agents are silanes, e.g. (3-Methacroyloxypropyl)trimethoxysilane. The fillers preferably have an average grain size <20 µm, preferably <5 µm and in particular <2 µm and an upper grain limit of 150 µm, preferably 70 µm and in particular 25 µm. Such fillers can be present in amounts of from about 3 to about 90 weight percent, especially about 25 to about 80 or about 50 to about 75 wt.-% of the composition.

Non-reinforcing fillers may also be used in the invention such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers also include reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used.

A combination of reinforcing and non-reinforcing fillers is particularly preferred. In this respect, the quantity of reinforcing fillers can vary from about 1 to about 10 wt.-%, and in particular, from about 2 to about 5 wt.-%.

The difference in the named overall ranges, i.e. about 2 to about 89 wt.-% is accounted for by non-reinforcing fillers.

Pyrogenically-prepared highly-disperse, silicic acids which have preferably been hydrophobized by surface treatment are preferred as reinforcing fillers. The surface treatment can be carried out, e.g. with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optionally components (D) like stabilizers, modifiers, dyes, pigments, thixotropic agents, flow improvers, or thinning agents, polymeric thickeners, surfactants, and diluting agent(s) can be added alone or in admixture as appropriate.

The above described carbosilane containing component (A) can be used as monomer in dental compositions that are curable preferably via radical polymerization of unsaturated groups, especially (meth)acrylate groups.

The dental composition of the invention can be used e.g. as dental filling material, crown and bridge material, veneer material, inlay or onlay.

The dental compositions of the invention can be provided as a 1 part mixture or as a 2 part mixture. This usually depends on the initiator used. If the initiator is light curing, the dental composition can be provided as a 1 part mixture, if the initiator is redox curing, the dental composition should be provided as a 2 part mixture.

Therefore, the present invention also relates to a kit of parts, comprising a base part (I) and a catalyst part (II), wherein the base part (I) comprises carbosilane containing component (A) and filler (C), and the catalyst part (II) comprises initiator (B), and wherein component (D) is present either in the base part or the catalyst part or in the base part and the catalyst part.

The dental compositions of the invention is usually packaged in a container or cartridge, preferably in a dental compule. Examples of such compules are described in U.S. Pat. No. 5,322,440 A1 or U.S. Pat. No. 4,391,590 or U.S. Pat. No. 5,165,890 . . . .

The present invention also relates to a method of using a dental composition comprising the steps of
a) providing the dental composition comprising carbosilane containing component (A) as described in the text;
b) applying the dental composition to a surface;
c) curing the dental composition.

The surface is usually a surface of a tooth, a crown or a bridge.

The present invention also relates to a method of producing a curable dental composition comprising the steps
a) providing components (A), (B), optionally (C) and optionally (D) as described above;
b) mixing the components of step a),
wherein component (A) is obtainable via hydrosilylation reaction.

The hydrosilylation reaction comprises reacting poly Si—H functional carbosilane component (i) and olefinic substituted (meth)acrylate moiety containing component (ii) as described above.

The invention is hereinafter described by examples. The examples are for illustrative purpose only and not intended to limit the invention.

The compounds listed in table 1 were prepared according to the references listed above and their refractive index and viscosity measured.

TABLE 1

| Examples of Compounds | Refractive Index | Viscosity [mPa * s] | Molecular Weight [g/mol] |
|---|---|---|---|
| Reference Compound 1: 1,3,5,7-Tetrakis-[3-(2-methacroyloxy-ethyloxy)-propyl]-1,3,5,7-tetramethyl-cyclotetrasiloxane | 1.465 | 100 | 921.3 |
| Example Compound 1: 2,2-Bis{3,5-bis[dimethyl-[3-(2-methacroyloxy-ethyloxy)-propyl]-silyl]-4-(3-methylbutyloxy)-phenyl}-propane | 1.505 | 1200 | 1282 |
| Reference Compound 2: Bis{dimethyl-[3-(2-methacroyloxy-ethyloxy)-propyl]-siloxy}-hexakis{dimethyl-[2-(5/6-methacroyloxy-bicyclo[2.2.1]hept-2-yl)-ethyl]-siloxy}-T8-silsesquioxane | 1.480 | 3700 | 2596 |
| Example Compound 2: 1-{Dimethyl-[3-(2-methacroyloxy-ethyloxy-propyl]-silyl}-6-{dimethyl-[2-(5/6-methacroyloxy-bicyclo[2.2.1]hept-2-yl)-ethyl]-silyl}-2-methoxy-naphthalene | 1.536 | 4700 | 651.0 |
| Example Compound 3: 2-{3-[Dimethyl-[2-(5/6-methacroyloxy-bicyclo[2.2.1]hept-2-yl)-ethyl]-silyl]-4-butyloxy-5-[dimethyl-[3-(2-methacroyloxy-ethyloxy)-propyl]-silyl]-phenyl}-2-{3-[dimethyl-[3-(2-methacroyloxy-ethyloxy)-propyl]-silyl]-4-butyloxy-phenyl}-propane | 1.521 | 11400 | 1061.7 |
| Example Compound 4: 1-{2,4,6-Tris[dimethyl-[2-(5/6-methacroyloxy-bicyclo[2.2.1]hept-2-yl)-ethyl]-silyl]-phenoxy}-3-{dimethyl-[2-(5/6-methacroyloxy-bicyclo[2.2.1]hept-2-yl)-ethyl]-silyl}-propane | 1.518 | 68000 | 1194 |

Dental compositions containing the carbosilane compounds according to the present invention as well as dental compositions containing state of the art reference compounds were prepared and their opacity measured.

TABLE 2

| Amounts in %-Weight | Examples of Dental Compositions | | | | | |
|---|---|---|---|---|---|---|
| | 1 | 2 | 3 | 4 | 5 | 6 |
| Reference Compound 1 | 29.9 | | | | | |
| Example Compound 1 | | 29.9 | | | | |
| Reference Compound 2 | | | 29.9 | | | |
| Example Compound 2 | | | | 29.9 | | |
| Example Compound 3 | | | | | 29.9 | |
| Example Compound 4 | | | | | | 29.9 |
| Bis(2,6-dichlorobenzoyl)-(4-butyl-phenyl)-phosphane oxide | 0.1 | 0.1 | 0.1 | 0.1 | 0.1 | 0.1 |
| Silaned Quartz, mean particle size <2 μm | 70.0 | 70.0 | 70.0 | 70.0 | 70.0 | 70.0 |
| Opacity [%] | 94.6 | 89.3 | 94.9 | 83.0 | 79.8 | 84.9 |
| Exact Height of Specimen [mm] | (3.5) | (3.6) | (3.5) | (3.5) | (3.5) | (3.7) |

The invention claimed is:
1. A dental composition comprising:
a) a carbosilane containing component comprising
at least one Si-Aryl bond,
at least one silicon atom,
at least one unsaturated moiety, and
no Si-Oxygen bond; and
b) an initiator;
wherein
the carbosilane containing component comprises a compound represented by the following formula (I):

B-D-E- {Aryl-[Si(A)$_a$(D-B)$_b$]$_n$}$_m$  (I)

wherein, independently selected from each other,
m is 1;
n is 1;
A is an aliphatic or cycloaliphatic moiety ($C_1$ to $C_6$) or aromatic moiety ($C_6$ to $C_{14}$);
B is a (meth)acrylate moiety attached onto spacer D;
D is an aliphatic or cycloaliphatic moiety (alkadiyl with $C_2$ to $C_{10}$), wherein C and/or H atoms can be substituted by O, Br, Cl, and Si atoms and which can comprise a bicyclic structural element;
E is a (cyclo)aliphatic moiety (alkadiyl with $C_5$ to $C_{11}$) wherein at least one C atom may be substituted by a Si atom and wherein other C and/or H atoms can be substituted by O, Br, Cl, and Si atoms;
Aryl is a $C_6$ to $C_{14}$ aromatic moiety;
a+b is 3;
a is 0, 1 or 2; and
b is 1, 2 or 3; and/or
the carbosilane containing component comprises a compound represented by the following formula (II):

{Aryl-[Si(A)$_a$(D-B)$_b$]$_n$}$_m$  (II)

wherein, independently selected from each other,
A is an aliphatic or cycloaliphatic moiety ($C_1$ to $C_6$) or aromatic moiety ($C_6$ to $C_{14}$);
B is a (meth)acrylate moiety attached onto spacer D;
D is an aliphatic or cycloaliphatic moiety (alkadiyl with $C_2$ to $C_{10}$), wherein C and/or H atoms can be substituted by O, Br, Cl, and Si atoms and which can comprise a bicyclic structural element;

Aryl is a $C_6$ to $C_{14}$ aromatic moiety;
a+b is 3;
a is 0, 1 or 2; and
b is 1, 2 or 3;
m is 1, and
n is 2, 3, 4, 5 or 6; and/or the carbosilane containing component comprises a compound represented by the following formula (III):

F- {Aryl-[Si(A)$_a$(D-B)$_b$]$_n$}$_m$  (III)

wherein, independently selected from each other,
A is an aliphatic or cycloaliphatic moiety ($C_1$ to $C_6$) or aromatic moiety ($C_6$ to $C_{14}$);
B is a (meth)acrylate moiety attached onto spacer D;
D is an aliphatic or cycloaliphatic moiety (alkadiyl with $C_2$ to $C_{10}$), wherein C and/or H atoms can be substituted by O, Br, Cl, and Si atoms and which can comprise a bicyclic structural element;
F is O or a (cyclo)aliphatic moiety (alkadiyl with $C_1$ to $C_{25}$) wherein C and/or H atoms can be substituted by O, Br, Cl, and Si atoms;

Aryl is a $C_6$ to $C_{14}$ aromatic moiety;
a+b is 3;
a is 0, 1 or 2;
b is 1, 2 or 3;
m is 2, 3 or 4,
n is 1, 2, 3, 4, 5 or 6; and/or
the carbosilane containing component comprises a compound represented by the following formula (IV):

G-{Aryl-[Si(A)$_a$(D-B)$_b$]$_n$}$_m$  (IV)

wherein, independently selected from each other,
A is an aliphatic or cycloaliphatic moiety ($C_1$ to $C_6$) or aromatic moiety ($C_6$ to $C_{14}$);
B is a (meth)acrylate moiety attached onto spacer D;
D is an aliphatic or cycloaliphatic moiety (alkadiyl with $C_2$ to $C_{10}$), wherein C and/or H atoms can be substituted by O, Br, Cl, and Si atoms and which can comprise a bicyclic structural element;
G is O or a (cyclo)aliphatic or aromatic or (cyclo)aliphatic aromatic or aromatic (cyclo)aliphatic moiety (diyl with $C_1$ to $C_{100}$) wherein C and/or H atoms can be substituted by O, Br, Cl, and Si atoms;

Aryl is a $C_6$ to $C_{14}$ aromatic moiety;
a+b is 3;
a is 0, 1 or 2;
b is 1, 2 or 3;
m is 2, 3 or 4,
n is 1, 2, 3, 4, 5 or 6; and/or the carbosilane containing component comprises a compound represented by the following formulas (IVa) and (IVb):

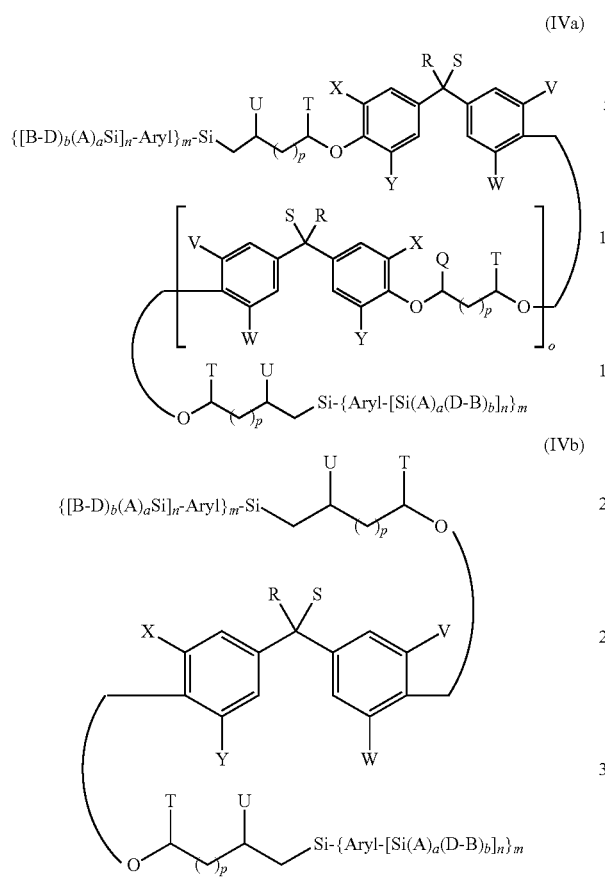

(IVa)

(IVb)

wherein, independently selected from each other,
A is an aliphatic or cycloaliphatic moiety ($C_1$ to $C_6$) or aromatic moiety ($C_6$ to $C_{14}$);
B is a (meth)acrylate moiety attached onto spacer D;
D is an aliphatic or cycloaliphatic moiety (alkadiyl with $C_2$ to $C_{10}$, wherein C and/or H atoms can be substituted by O, Br, Cl, and Si atoms and which can comprise a bicyclic structural element;

Aryl is a $C_6$ to $C_{14}$ aromatic moiety;
a+b is 3;
a is 0, 1 or 2;
b is 1, 2 or 3;
m is 1, 2, 3 or 4;
n is 1, 2, 3, 4, 5 or 6;
p is 0, 1, 2, 3 or 4;
o is 0, 1, 2, 3, 4 or 5;
Q is H, $CH_3$;
each of R and S is H, methyl, ethyl, phenyl or alkadiyl $C_5$ to $C_8$;
each of T and U is H, methyl or ethyl; and
each of V, W, X and Y is H, Br, Cl or F.

2. The dental composition of claim 1, further comprising a filler.

3. The dental composition of claim 2, further comprising an additive selected from modifiers, dyes, pigments, thixotropic agents, flow improvers, polymeric thickeners, surfactants, odorous substances, diluting agents, and flavourings.

4. The dental composition of claim 1, wherein the carbosilane containing component has a refractive index above 1.500.

5. The dental composition of claim 1, wherein the carbosilane containing component has a viscosity above 0.1 Pa*s.

6. The dental composition of claim 1, wherein the carbosilane containing component has a molecular mass above 500.

7. The dental composition of claim 1, wherein the opacity of the cured composition is above 10%.

8. The dental composition of claim 1, wherein the compressive strength of the cured composition is equal to or above 150 MEPa.

9. The dental composition of claim 1, wherein the flexural strength of the cured composition is equal to or above 50 MPa.

10. The dental composition of claim 3, wherein the carbosilane containing component is present in an amount of at least 1% by weight, the initiator is present in an amount of at least 0.01% by weight, the filler is present in an amount of at least 3% by weight, and the additive is present in an amount of less than 25% by weight, with respect to the whole composition.

11. The dental composition of claim 1, wherein the carbosilane containing component is selected from

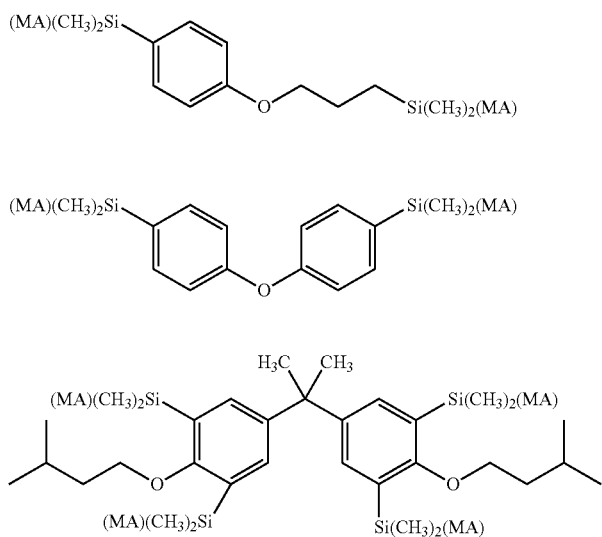

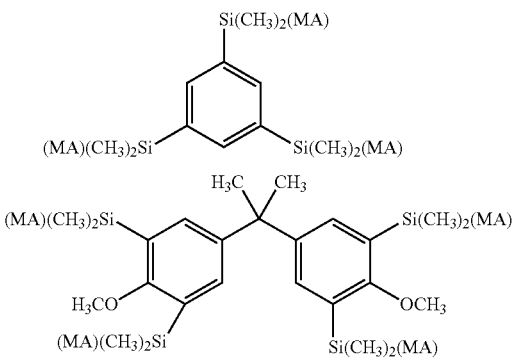

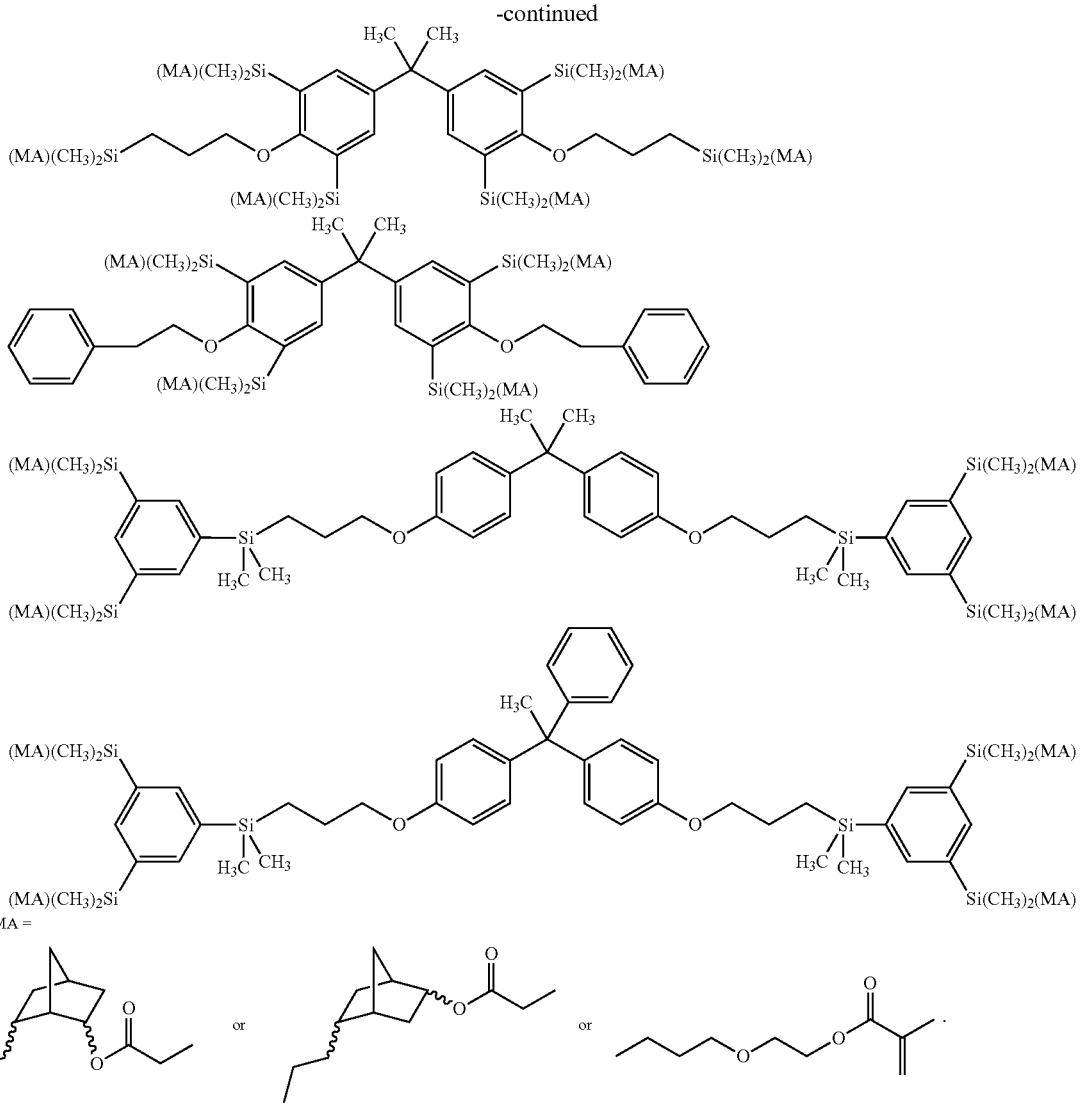

12. The dental composition of claim 1, wherein the initiator comprises a light curing initiator or a redox curing initiator or a combination of both.

13. The dental composition of claim 2, wherein the filler comprises reinforcing and/or non-reinforcing fillers.

14. A cartridge or container filled with the dental composition of claim 1.

15. A kit of parts, comprising a base part and a catalyst part, wherein the base part comprises the carbosilane containing component of claim 1, and the catalyst part comprises an initiator, and wherein a filler component and an additive are present either in the base part or the catalyst part or in the base part and the catalyst part.

16. A method of producing the dental composition of claim 1, the method comprising the steps of:
    a) providing the carbosilane containing component and the initiator of claim 1; and
    b) mixing the compounds of step a), wherein the carbosilane containing component is obtained via a hydrosilylation reaction.

17. The method according to claim 16, wherein the hydrosilylation reaction comprises reacting a poly Si-H functional carbosilane component with an olefnic substituted (meth)acrylate moiety containing component.

18. A dental material selected from a dental filling material, a crown or bridge material, a veneer material, an inlay and/or an onlay, wherein the material comprises the composition of claim 1.

19. A method for preparing a dental material comprising the steps of:
    a) providing the dental composition of claim 1;
    b) applying the dental composition to a surface; and
    c) curing the dental composition.

* * * * *

UNITED STATES PATENT AND TRADEMARK OFFICE
CERTIFICATE OF CORRECTION

PATENT NO. : 7,915,324 B2  
APPLICATION NO. : 11/572069  
DATED : March 29, 2011  
INVENTOR(S) : Adrian Eckert It is certified that error appears in the above-identified patent and that said Letters Patent is hereby corrected as shown below:

On Title page Other Publications  
Column 2  
Line 8, Delete "Hydosilylation," and insert -- Hydrosilylation, --, therefor.  
Line 13, Delete "Hydrosilylation,p107ff.," and insert -- Hydrosilylation, p107ff., --, therefor.

Column 1  
Line 37, Delete "1methylethyl)" and insert -- 1-methylethyl) --, therefor.

Column 4  
Line 8, Delete "composition" and insert -- composition. --, therefor.

Column 5  
Line 22, Delete "know" and insert -- known --, therefor.

Column 20  
Line 57 (Approx.), Delete "A=$C_1$, a=2b=m=2, n=2G=$C_3$," and insert -- A=$C_1$, a=2, b=1, m=2, n=2, G=$C_3$, --, therefor.

Column 23  
Line 1 (Structure IVa), Delete "{[B-D)$_b$" and insert -- {[(B-D)$_b$ --, therefor.

Signed and Sealed this  
Fourteenth Day of February, 2012

David J. Kappos  
*Director of the United States Patent and Trademark Office*

CERTIFICATE OF CORRECTION (continued)
U.S. Pat. No. 7,915,324 B2

Column 25
Lines 50-62 (Approx.), (Structure IVb),

Delete " 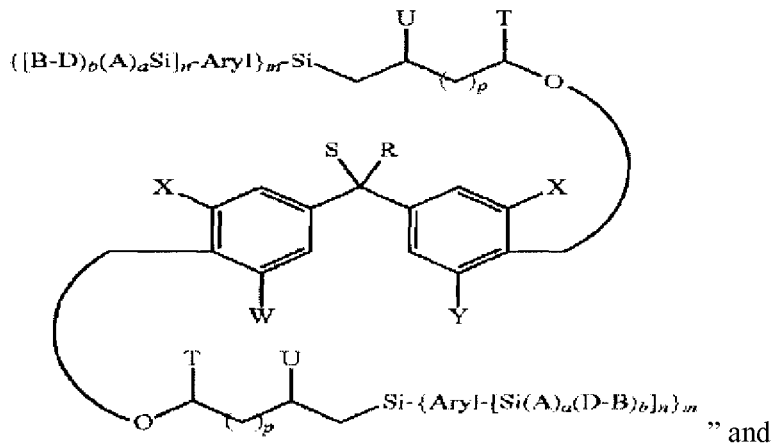 " and insert -- 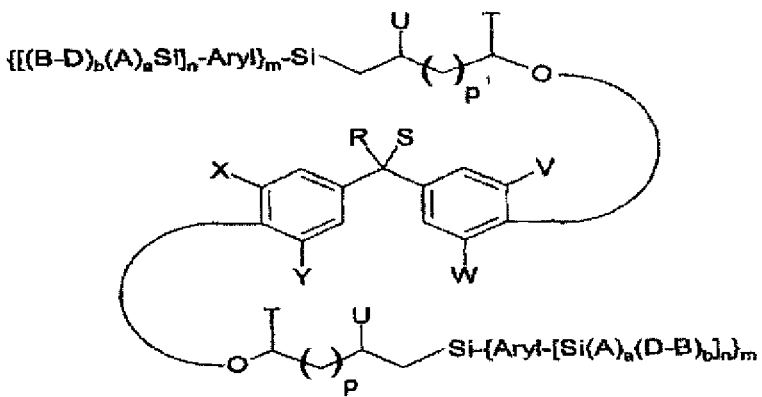 --, therefor.

Column 27
Line 15 (Approx.), Delete "a 2," and insert -- a=2, --, therefor.

Column 44
Line 57, Delete "moleculer" and insert -- molecular --, therefor.

Column 49
Line 6 (Approx.), (Structure IVa), In Claim 1, delete "{[B-D)b" and insert -- {[(B-D)b --, therefor.
Line 20 (Approx.), (Structure IVb), In Claim 1, delete "{[B-D)b" and insert -- {[(B-D)b --, therefor.
Line 41, In Claim 1, delete "$C_{10}$," and insert -- $C_{10}$,) --, therefor.

Column 50
Line 31, In Claim 8, delete "MEPa." and insert -- MPa. --, therefor.

CERTIFICATE OF CORRECTION (continued)
U.S. Pat. No. 7,915,324 B2

Column 51
Lines 40-43 (Approx.),
In Claim 11, delete

" 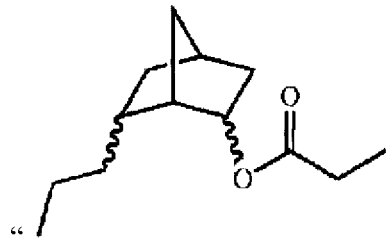 or 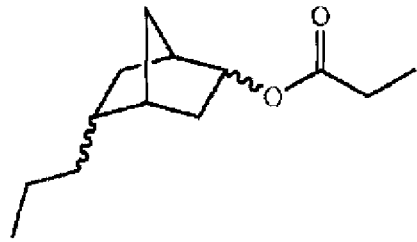 " and insert -- 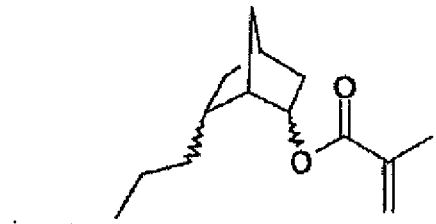 or 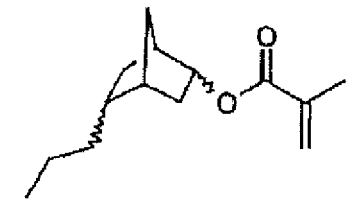 --, therefor.

Column 52
Line 50 (Approx.), In Claim 17, delete "olefnic" and insert -- olefinic --, therefor.